(12) United States Patent
Leis et al.

(10) Patent No.: US 11,666,562 B2
(45) Date of Patent: Jun. 6, 2023

(54) ILAPRAZOLE FOR INHIBITING THE RELEASE OF ENVELOPED VIRUSES FROM CELLS

(71) Applicant: Northwestern University, Evanston, IL (US)

(72) Inventors: Jonathan Leis, Chicago, IL (US); Chi-Hao Luan, Evanston, IL (US)

(73) Assignee: Northwestern University, Evanston, IL (US)

( * ) Notice: Subject to any disclaimer, the term of this patent is extended or adjusted under 35 U.S.C. 154(b) by 104 days.

(21) Appl. No.: 17/301,454

(22) Filed: Apr. 2, 2021

(65) Prior Publication Data

US 2021/0308114 A1    Oct. 7, 2021

Related U.S. Application Data

(60) Provisional application No. 63/014,104, filed on Apr. 22, 2020, provisional application No. 63/004,040, filed on Apr. 2, 2020.

(51) Int. Cl.
| | |
|---|---|
| A61K 31/4439 | (2006.01) |
| A61P 31/18 | (2006.01) |
| A61P 31/22 | (2006.01) |
| A61P 31/14 | (2006.01) |

(52) U.S. Cl.
CPC .......... *A61K 31/4439* (2013.01); *A61P 31/14* (2018.01); *A61P 31/18* (2018.01); *A61P 31/22* (2018.01)

(58) Field of Classification Search
CPC ............................ A61K 31/4439; A61P 31/14
See application file for complete search history.

(56) References Cited

U.S. PATENT DOCUMENTS

| | | | |
|---|---|---|---|
| 6,262,086 B1 | 7/2001 | Whittle et al. | |
| 6,852,739 B1 | 2/2005 | Garvey | |
| 10,300,080 B2 | 5/2019 | Leis | |
| 10,765,687 B2 | 9/2020 | Leis | |
| 2002/0077276 A1 | 6/2002 | Fredeking et al. | |

(Continued)

FOREIGN PATENT DOCUMENTS

| | | |
|---|---|---|
| CN | 111084886 A | 5/2020 |
| EP | 0187977 A1 | 7/1986 |

(Continued)

OTHER PUBLICATIONS

Chen et al. "TSG101: A Novel anti-HIV-1 drug target," Current Medicinal Chemistry, 2010, vol. 17, No. 9, pp. 750-758 (Year: 2010).*

(Continued)

*Primary Examiner* — Shengjun Wang

(74) *Attorney, Agent, or Firm* — Quarles & Brady LLP

(57) ABSTRACT

Disclosed are methods and compositions for treating an infection by an enveloped virus in a patient in need thereof. The methods include administering to the patient a compound that inhibits or blocks release of the enveloped virus from an infected cell. As such, the disclosed methods include methods of inhibiting or blocking release of an enveloped virus from a cell. The disclosed methods may include administering to the patient a prazole-type compound having a substituted (pyridin-2-yl)methylsulfinylbenzimidazole core.

20 Claims, 10 Drawing Sheets

Specification includes a Sequence Listing.

(56) References Cited

U.S. PATENT DOCUMENTS

| | | |
|---|---|---|
| 2006/0217423 A1 | 9/2006 | Deng et al. |
| 2011/0262442 A1 | 10/2011 | Hamilton et al. |
| 2014/0179637 A1 | 6/2014 | Leis |
| 2015/0238472 A1 | 8/2015 | Ghebremariam et al. |
| 2016/0319252 A1 | 11/2016 | Bong et al. |
| 2017/0095485 A1 | 4/2017 | Leis et al. |
| 2019/0209589 A1 | 7/2019 | Leis |
| 2020/0368258 A1 | 11/2020 | Leis |
| 2021/0308114 A1 | 10/2021 | Leis et al. |

FOREIGN PATENT DOCUMENTS

| | | |
|---|---|---|
| WO | 2005004921 A1 | 1/2005 |
| WO | 2016029146 A1 | 2/2016 |

OTHER PUBLICATIONS

Leis et al. "Ilaprazole and other novel prazole-based compounds that bind TSG101 inhibit viral budding of herpes Simplex virus 1 and 2 and human immunodeficiency virus from cells," J. Virology, 2021, vol. 95, Issue 11, e00190-21 (Year: 2021).*

Al-Bari, "Targeting endosomal acidification by chloroquine analogs as a promising strategy for the treatment of emerging viral diseases." Pharmacology Research & Perspectives, vol. 5, Issue 1, pp. 1-13, 2017.

Almario et al., "Increased Risk of COVID-19 Among Users of Proton Pump Inhibitors." The American Journal of Gastroenterology, vol. 00, 2020, Pages.

Arii et al., "ESCRT-III mediates budding across the inner nuclear membrane and regulates its integrity." Nature Communications, 9, article 3379, 2018.

Arumi, Y., Kuroki, M., Maki, M., Ikeda, M., Dansako, H., Wakita, T. and Kato, N. "The ESCRT system is required for hepatitis C virus production," PLoS One, vol. 6, pp. 1-10, 2011.

Calistri et al., 2015. Functional Interaction Between the ESCRT-I Component TSG101 and the HSV-1 Tegument Ubiquitin Specific Protease. Journal of cellular physiology 230:1794-1806.

Corless et al., "Vps4 and the ESCRT-III complex are required for the release of infectious hepatitis C virus particles," Journal General Virology, vol. 91, pp. 362-372, 2010.

Erlich et al., Activation of the Inositol (1,4,5)-triphosphate calcium gate receptor is required for HIV-1 Gag release. J. Virol. 84, 6438-6451 (2010).

Han et al., Small molecule probes targeting the viral PPxY-host Nedd4 interface block egress of a broad range of RNA viruses. J. Virol. vol. 88, pp. 7294-7306, 2014.

Kikonyogo et al., "Proteins related to the Nedd4 family of ubiquitin protein ligases interact with the L domain of Rous sarcoma virus and are required for Gag budding from cells," Proceedings National Academy Science USA, vol. 98, pp. 11199-11204, 2001.

Kuang et al., "The mechanism of Inhibition of retrovirus release from cells by interferon induced gene ISG15," Journal Virology, vol. 85, pp. 7153-7161, 2011.

Lee et al., 2012. The ESCRT machinery is recruited by the viral BFRF1 protein to the nucleus-associated membrane for the maturation of Epstein-Barr Virus. PLoS Pathog 8:e1002904.

Leis et al., "Ilaprazole and other novel prazole-based compounds that bind Tsg101 and inhibit viral budding of HSV-1/2 and HIV from cells," J. Virol. Mar. 17, 2021; 1-20.

Lo et al., "Evaluation of fluorescence-based thermal shift assays for hit identification in drug discovery," Anal Biochem. (2004) 332:153-159.

Lu et al., "A host-oriented inhibitor of Junin Argentine Hemorrhagic Fever Virus egress" Journal of Virology, vol. 88, p. 4736, 2014.

Luan et al., "Ligand screening using Fluorescence Thermal Shift Analysis (FTS)," Structural Genomics and Drug Discovery: Methods and Protocols, Methods Mal. Biol. 2013, Chapter 20, pp. 263-285 (W.F. Anderson, ed.) Humana Press.

Luan et al., 2014. Ligand screening using fluorescence thermal shift analysis (FTS), p. 263-289, Structural Genomics and Drug Discovery. Springer.

Maran et al., J. Coll. Gen. Practit, 1967, 13: 110-114 (Year: 1967).

Medina et al., 2008. Tsg101 can replace Nedd4 function in ASV Gag release but not membrane targeting. Virology 377:30-38.

Medina et al., 2005. The functionally exchangeable L domains in RSV and HIV-1 Gag direct particle release through pathways linked by Tsg101. Traffic 6:880-894.

Myoung et al., "Generation of a doxycycline-inducible KSHV producer cell line of endothelial origin: maintenance of tight latency with efficient reactivation upon induction," J. Viral. Methods (2011) 174(1-2):12-21.

Pantoliano et al., "High-density miniaturized thermal shift assays as a general strategy for drug discovery," J. Biomol. Screen {2001) 6(6):429-440.

Pincetic et al., The interferon-induced gene ISG15 blocks retrovirus release from cells late in the budding process. Journal Virology, vol. 84, pp. 4725-4736, 2010.

Pinetic et al., 2009. The Mechanism of Budding of Retroviruses From Cell Membranes. Adv Virol 2009:6239691-6239699.

Pincetic et al., "Avian sarcoma virus and human immunodeficiency virus, type 1 use different subsets of ESCRT proteins to facilitate the budding process," Journal Biological Chemistry, vol. 283, pp. 29822-29830, 2008.

Pornillos et al., "Structure and functional interactions of Tsg101 UEV domain." Embo J. 21, pp. 2397-2406, 2002.

Seo et al., Budding of Enveloped Viruses; Interferon induced ISG15-Antivirus Mechanisms Targeting the Release Process. In Advances in Virology, Hindawi Publishing Company vol. 2012, pp. 1-10.

Sette et al., "The ESCRT-associated protein Alix recruits the ubiquitin ligase Nedd4-1 to facilitate HIV-1 release through the LYPXnL L domain motif." J Virol. 84 (16), 8181-8192, 2010.

Shin et al., 2013. Pharmacokinetics and pharmacodynamics of the proton pump inhibitors. J Neurogastroenterol Motil 19:25-35.

Strickland et al., "Tsg101 Chaperone Function Revealed By HIV-1 Assembly Inhibitors." Nature, Communications, 8, 1391, 2017.

Timmins et al., "Ebola virus matrix protein VP40 interaction with human cellular factors Tsg101 and Nedd4," Journal Molecular Biology, vol. 326, pp. 493-502, 2003.

Tomas et al. EGF receptor trafficking: consequences for signaling and cancer. Trends Cell Biol 24, 26-34 (2014).

Vana et al., "The role of Nedd4 and ubiquitination of RSV Gag in budding of virus-like particles from cells," Journal Virology, vol. 78, pp. 13943-13953, 2004.

Verplank et al., "Tsg101, the prototype of a class of dominant-negative ubiquitin regulators, binds human mmunodeficiency virus type 1 Pr55Gag: the L domain is a determining of binding," Proceedings National Academy Science USA, vol. 98, pp. 7724-7729, 2001.

Vieira et al., "Use of the red fluorescent protein as a marker of Kaposi's sarcoma-associated herpes virus lytic gene expression," Virology (2004) 325(2):225-40.

Watanabe et al., 2020. Selective Targeting of Virus Replication by Proton Pump Inhibitors. Sci Rep 10:4003.

Wills, J., Cameron, C., Wilson, C., Xiang, Y., Bennett, R., and Leis, J. "An assembly domain of Rous sarcoma virus Gag protein required late in budding," Journal Virology, vol. 68, pp. 6605-6618, 1994.

Zhang et al., "Patterns of microRNA expression characterize stages of human B-cell differentiation," Blood (2009) 113(19):4586-4594.

International Search Report and Written Opinion issued in International Application No. PCT/US2021/070450, dated Aug. 13, 2021.

* cited by examiner

| Peptide conc (μM) | Free CRISPR2 Media 2h | Free CRISPR2 Media 4h | CRISPR2 Media 24h | Free CRISPR2 Media 4h | Free CRISPR2 Media 6h | Viability OD(Cl...) |
|---|---|---|---|---|---|---|
| 0 | 2.50E+05 | 2.80E+05 | 4.70E+07 | 8.0E+07 | 8.50E+06 | 1.694 |
| B2 | 2.90E+05 | 6.50E+04 | 4.00E+06 | 1.4E+07 | 1.30E+06 | 1.724 |
| 33 | N.D. | 1.00E+03 | 2.30E+04 | N.D. | 5.60E+04 | 1.759 |
| 55 | 1.30E+05 | 2.50E+02 | 1.50E+03 | 8.0E+06 | 4.80E+03 | 1.742 |
| 18 | 5.40E+04 | 0.00E+00 | 6.00E+02 | 5.3E+05 | 1.80E+02 | 1.777 |
| B8 | 2.40E+03 | 0.00E+00 | 3.00E+02 | 3.5E+04 | N.D. | 1.714 |
|    | 1.30E+02 | N.D. | N.D. | 1.0E+02 | N.D. | N.D. |
| ABX | N.D. | N.D. | N.D. | N.D. | N.D. | 0.872 |

Fig. 5

| Prazole compound | EC₅₀ (μM) Inhibition of HSV-2 Budding at 24h | Structure |
|---|---|---|
| Omeprazole-N-Oxide | - | 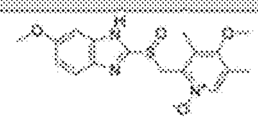 |
| Pantoprazole | - | 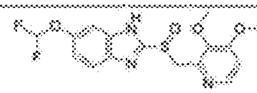 |
| Esomeprazole | 140 | 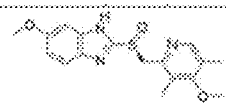 |
| Lansoprazole | 84 | 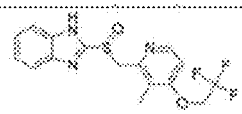 |
| Omeprazole | 78 | 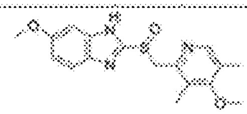 |
| Dexlansoprazole | 76 | 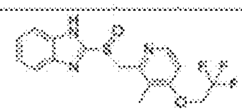 |
| Tenatoprazole | 84 | 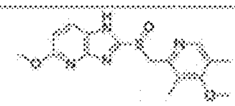 |
| 4-Desmethoxy-omeprazole | 52 | 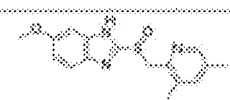 |
| Rabeprazole | - | 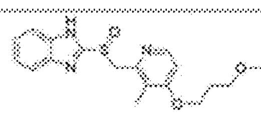 |
| Ilaprazole | 3-9 | 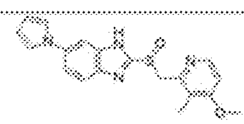 |

| Itraconazole (μM) | Titer of HSV-1 in media 24h | Titer of HSV-1 in media 48h | Titer of HSV-1 in media 72h | Total HSV-1 in media + cell lysate 24h | Titer of HSV-2 in media 24h | Total HSV-2 in media + cell lysate 24h | Titer of HSV-2 in media 48h |
|---|---|---|---|---|---|---|---|
| 0 | 3.00E+06 | 3.90E+07 | 1.00E+08 | 2.3E+08 | 2.80E+03 | 1.20E+07 | 1.00E+06 |
| 4.5 | 2.00E+06 | 2.40E+06 | 9.00E+05 | 7.0E+07 | 1.00E+03 | 3.60E+07 | 2.50E+05 |
| 9.0 | 7.50E+04 | 2.50E+05 | 2.20E+05 | 3.6E+06 | 5.00E+04 | 4.50E+06 | 7.50E+04 |
| 13.5 | 3.20E+04 | 2.00E+02 | 4.50E+02 | 3.8E+05 | 1.00E+04 | 4.30E+06 | 5.50E+04 |
| 18.0 | 6.00E+02 | 0.00E+00 | 1.00E+02 | 9.1E+03 | 1.50E+03 | 2.00E+05 | 1.50E+03 |
| 22.5 | 1.00E+02 | 0.00E+00 | N.D. | 7E+02 | 1.00E+02 | 1.50E+04 | 3.00E+02 |
| 54 | N.D. | N.D. | N.D. | N.D. | N.D. | N.D. | N.D. |
| 270 | N.D. | N.D. | N.D. | N.D. | N.D. | N.D. | N.D. |

| Ilaprazole (μM) | 96® Cell Viability OD$_{450nm}$, 24h | WST-1 Cell Toxicity OD$_{450}$, 24h |
|---|---|---|
| 0 | 1.694 | 0.993 |
| 4.5 | 1.764 | 1.058 |
| 9.0 | 1.711 | 1.055 |
| 13.5 | 1.690 | 0.950 |
| 18.0 | 1.737 | N.D. |
| 27 | N.D. | 1.055 |
| 54 | 1.658 | N.D. |
| 270 | 0.466 | 0.423 |

ILAPRAZOLE FOR INHIBITING THE RELEASE OF ENVELOPED VIRUSES FROM CELLS

CROSS-REFERENCE TO RELATED PATENT APPLICATIONS

This application claims the benefit of priority under 35 U.S.C. § 119(e) to U.S. Provisional Application No. 63/004,040, filed on Apr. 2, 2020, and U.S. Provisional Application No. 63/014,104, filed on Apr. 22, 2020, which contents are incorporated herein by reference in their entireties.

REFERENCE TO A SEQUENCE LISTING SUBMITTED VIA EFS-WEB

A Sequence Listing accompanies this application and is submitted as an ASCII text file of the sequence listing named "702581_01929_ST25.txt" which is 28 KB in size and was created on Mar. 31, 2021. The sequence listing is electronically submitted via EFS-Web with the application and is incorporated herein by reference in its entirety.

FIELD

The invention relates to methods and compositions for blocking the release of enveloped viruses from cells. In particular, the invention relates to methods of administering Ilaprazole to treat and/or prevent viral infection and/or disease.

BACKGROUND

There is considerable interest developing antiviral reagents to combat viral infections. The two most prevalent antiviral strategies focus on creating immunity to viral infection by use of vaccines or by interfering with a necessary virus-specific process essential to virus maintenance, replication and propagation in the host.

Vaccines have been successfully developed for many viruses to combat viral infections. So-called live vaccines containing attenuated version(s) of the target virus provide a convenient means of conferring immunity as typically only one inoculation is required. The drawbacks to most live virus vaccines lie in their limited shelf life, the requirement for maintaining appropriate storage conditions to preserve the vaccine reagent, and the possibility of live attenuating virus vaccines reverting to high virulence due to their active replication. These drawbacks can be avoided by using so-called inactivated virus vaccines containing a completely inert virus particle or a sub-viral component like a protein. The drawback to inactive viral vaccines is that multiple inoculations are required to confer full immunity. Furthermore, vaccines have an attendant risk that adverse reactions might arise in certain populations following immunization (for example, autoimmunity responses associated with Guillain-Barre syndrome (GBS)).

Antiviral compounds that specifically target a viral replication process have also proven effective for treating some virus infections. Examples of such reagents include small molecule inhibitors selective for a given viral protein, such as a viral replicase (e.g., the nucleoside analog 3'-azidothymidine for inhibiting the HIV-1 reverse transcriptase) or a viral protease (e.g., Darunavir for inhibiting HIV-1 protease). Owing to their small molecular size and chemical composition, antiviral compounds can be formulated as pharmaceutical compositions having significant shelf-life and can typically retain their potency over a larger temperature range during storage than many vaccines. However, HIV-1 and other virus can mutate to escape the effectiveness of the antiviral drugs when such drugs are targeted against virus-specific proteins. In particular, HIV-specific drugs have side-effects that cause patients to interrupt therapy that can lead to drug-resistant viral strains.

Generally, antiviral compounds are typically used in combinations for maximum efficacy and durability. Though most aspects of the viral replication process are susceptible to targeting and inhibition, the primary focus of antiviral inhibitor drug development is on early stage processes of viral replication, when the copy number of viral protein or nucleic acid targets is relatively low.

Late stage replication events include those associated with virus particle assembly and release from the host cell. These viral processes are more difficult targets to develop antiviral reagents. This is due in part to the vastly larger number of virus particles that result from active viral replication.

Enveloped virus particles adopt an outer membrane structure composed of the host cell membrane in its final virus form. Examples of enveloped viruses include retroviruses (e.g., human immunodeficiency virus, type 1), rhabdoviruses (e.g., rabies virus), and herpes viruses (e.g., herpes simplex virus, type 1). For enveloped viruses, the final stages of virus replication include envelope maturation, budding and release from an infected cell.

No antiviral therapeutic reagents have been developed that target the processes of enveloped virus budding and release. This is due in large part to the inability to target virus-specific proteins, owing to the large number of viral proteins present during late phase infection. But more importantly, the host cell-virus interactions responsible for enveloped virus particle maturation, budding and release are only poorly understood.

Here, we demonstrate that prazole-type drugs can be utilized to inhibit the release of enveloped viruses from infected cells. In particular, we demonstrate that prazole-type drugs such as Ilaprazole, can be utilized to inhibit the release of enveloped viruses from infected cells, including lentivirus such as human immunodeficiency virus and herpes viruses such as human herpes virus type 1 and human herpes virus type 2.

SUMMARY

Disclosed are methods and compositions for treating an infection by an enveloped virus in a patient in need thereof. The methods include administering to the patient a compound that inhibits or blocks release of the enveloped virus from an infected cell. As such, the disclosed methods include methods of inhibiting or blocking release of an enveloped virus from a cell.

In some embodiments, the disclosed methods comprise administering to the patient a prazole-type compound having a substituted (pyridin-2-yl)methylsulfinyl-benzimidazole core. Suitable prazole-type compounds may include a compound of a formula:

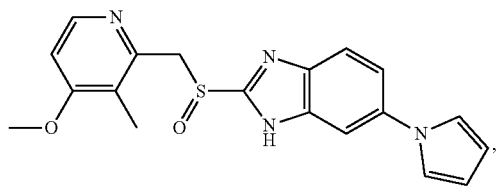

which otherwise is referred to as 2-[(4-methoxy-3-methylpyridin-2-yl)methylsulfinyl]-6-pyrrol-1-yl-1H-benzimidazole or Ilaprazole.

BRIEF DESCRIPTION OF THE FIGURES

FIG. 4. Inhibitory effect of Ilaprazole on HSV-2 and HSV-1 production. Vero cells infected with HSV-2 or HSV-1 at MOI of 0.1 and examined by transmission electron microscopy 24 h later. HSV-2 infected untreated cells (A & B) and cells treated with 18 µM ilaprazole (C & D). HSV-1 infected untreated cells (E & F) and cells treated with 18 µM ilaprazole (G & H). Eighty cells where virus particles were observed were examined. In the presence of ilaprazole, we observe no or very few particles in the cytoplasm. Treated cells also have an accumulation of electron dense material and particles associated with them. In untreated HSV-2 infected cells, we observed an average of 120 particles ranging from 28-204 in the nucleus, and an average of 16 particles ranging from 10-22 in the nucleus. In treated HSV-2 infected cells, we observed 0 particles in the cytoplasm and an average of 31 particles ranging from 9-56 in the nucleus. In untreated HSV-1 infected cells we observed an average of 135 particles ranging from 12-152 in the cytoplasm, and an average of 35 particles ranging from 10-66 in the nucleus. In treated HSV-1 infected cells, we observed 0 particles in the cytoplasm and an average of 43 particles ranging from 15-166 in the nucleus. Arrows point to virus particles. Nuc, nucleus. Cyt, cytoplasm.

FIG. 5. Table 1. Effect of Tenatoprazole on HSV-1 and -HSV-2 release from Vero cells. Tenatoprazole was incubated with Vero cells infected with HSV-1 or HSV-2 at a range of concentrations. The virus released into the media fraction at stated times was determined as described in Materials and Methods. Total virus is the amount of virus released from cells plus virus inside of the cells. Viability of Vero cells incubated with increased concentration of tenatoprazole was determined using the 96® AQueous One Solution cell proliferation assay reagent as described in Materials and Methods. Total titer for HSV-1 was not included. Duplicate plaque assays of 10-fold serial dilutions were determined with an average of less than 13% difference in the number of plaques counted. The 24 h, 48 h data were repeated 6 times each. The total virus was repeated twice. The data presented is the average of 2 experiments where the titers varied between 5 to 20%.

FIG. 7. Table 3A and 3B. Effect of Ilaprazole on release of HSV-1 and HSV-2 from Vero cells. Different concentrations of ilaprazole were incubated for the times indicated with HSV-1 or HSV-2 infected cells similar to that described in the legend to Table 1. Virus titer released into the media and total virus was determined. Viability of Vero cells incubated with increased concentration of tenatoprazole was determined using the 96® AQueous One Solution cell proliferation assay reagent as described in Materials and Methods. Data were analyzed as described in legend to Table 1 and experiments were repeated 4 times each.

DETAILED DESCRIPTION

Figure 1:
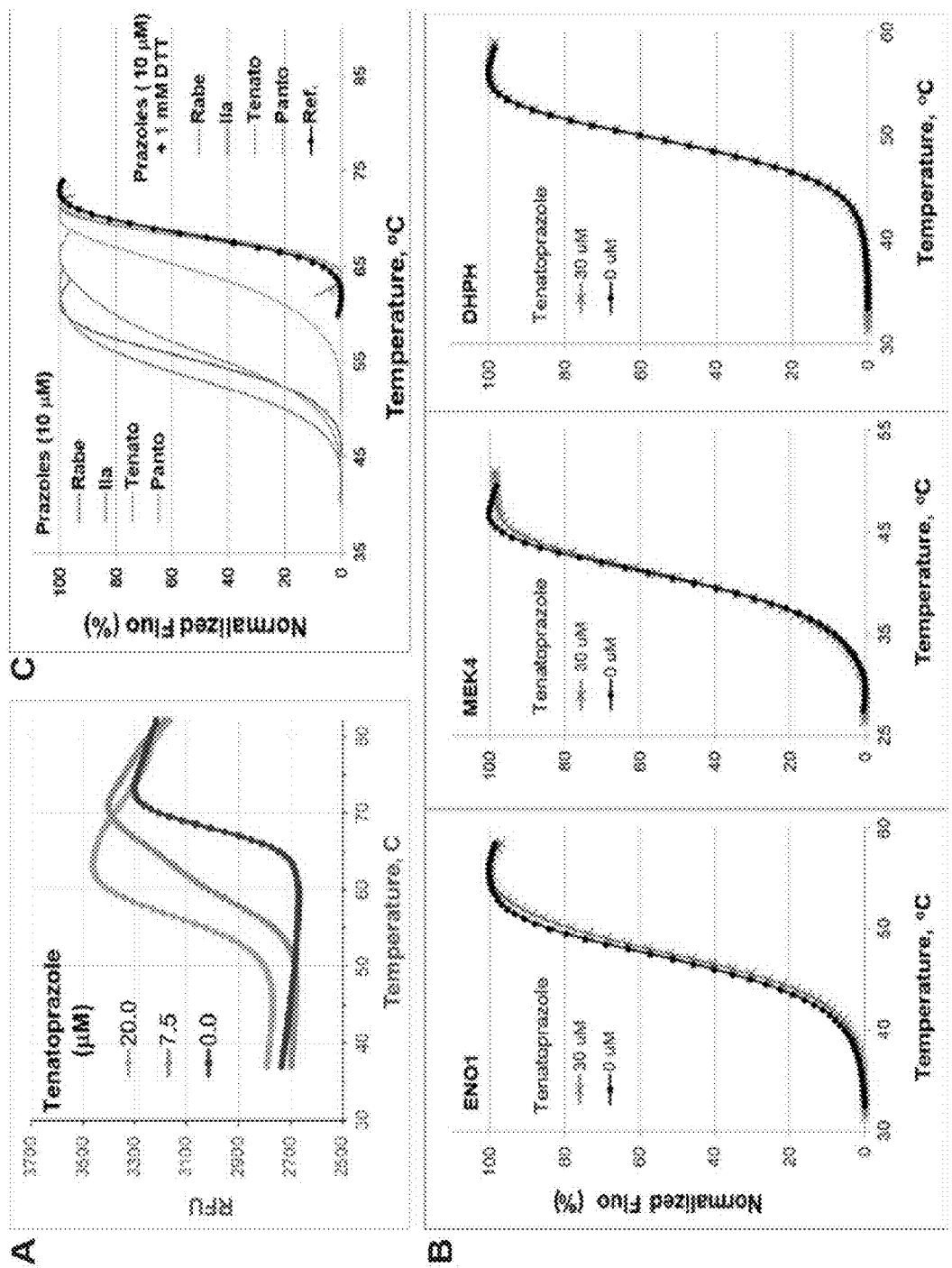
FIG. 1. Thermal shift data of Tsg101 by lead compound Tenatoprazole (N16). (A) The compound caused a dose-dependent shift in the Tm for Tsg101-UEV indicating binding to the key domain of Tsg101 as described in Materials and Methods. (B) Thermal shift data of three human proteins, DHPH, ENO1, and MEK4 not related to Tsg101 by lead compound tenatoprazole. The effect of the prazole compound on the thermal stability of these three proteins is negligible, indicating that the dramatic modulation of the thermal transition of Tsg101 by the prazoles is due to specific interaction. (C) The addition of DTT abolishes the Tm shift in the FTS assay, consistent with prazole compounds forming a disulfide bond to Tsg101. Rabe: Rabeprazole, Ila: Ilaprazole, Tenato: tenatoprazole, Panto: pantoprazole, ref: reference.

Disclosed are methods and compositions for treating viral infections. The methods and compositions are described herein using several definitions, as set forth below and throughout the application.

As used in this specification and the claims, the singular forms "a," "an," and "the" include plural forms unless the context clearly dictates otherwise. For example, "a therapeutic agent" should be interpreted to mean "one or more therapeutic agents" unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The presently disclosed methods and compositions relate to therapeutic treatment of subjects in need thereof. As used herein, the term "subject," which may be used interchangeably with the terms "patient" or "individual," refers to one who receives medical care, attention or treatment and may encompass a human patient. As used herein, the term "patient" is meant to encompass a person who has a viral infection or is at risk for developing a viral infection, which includes but is not limited to, viral infections associated with virus that are enveloped and that are released from infected cells.

As used herein, the phrase "effective amount" shall mean that drug dosage that provides the specific pharmacological response for which the drug is administered in a significant number of subject in need of such treatment. An effective amount of a drug that is administered to a particular subject in a particular instance will not always be effective in treating the conditions/diseases described herein, even though such dosage is deemed to be a therapeutically effective amount by those of skill in the art.

As used herein, the term "modulate" means decreasing or inhibiting activity and/or increasing or augmenting activity. Modulating viral release may mean decreasing viral release from a cell.

Inhibition of Viral Release from Infected Cells

Disclosed herein are methods and composition to inhibit the interaction of cellular proteins or fragments thereof with L domain-containing peptides of enveloped viruses. In particular, the methods and compositions may be utilized to inhibit the interaction of cellular proteins or fragments thereof, such as TSG101 or a fragment thereof or a Nedd 4-related family peptide or a fragment thereof, with L domain-containing peptides of enveloped viruses. The present inventors have determined that enveloped viruses use cellular pathways for mediating virus budding and that inhibiting these pathways results in significantly decreased rates of enveloped virus release from cell surfaces. The methods disclosed herein provide a robust, high-throughput approach to identify lead compounds having potent inhibitory effects on enveloped virus protein interactions with the components of these pathways and, thereby, virus particle release. Such methods offer a common mechanism to target a broad spectrum of viruses with a general anti-viral single therapeutic agent.

Enveloped viruses such as retroviruses and lentiviruses (e.g., avian sarcoma and leukosis virus (ASLV) and human immunodeficiency virus, type 1 (HIV-1)) include late assembly domains ("L-domains") encoded within their Gag protein sequence that interact with cellular components of the endosomal sorting complex required for transport ("ESCRT") machinery for virus budding and release from cells.

The L-domains have been identified in a variety of enveloped viruses and families of enveloped viruses. A consensus subset of L-domain motifs that interact with the critical ESCRT-dependent processes that enveloped viruses use to bud from cell membranes is known. (See U.S. Publication Nos. 2014/0179637 and 2017/0095485, the contents of which are incorporated herein by reference in their entireties).

One of these L-domain motifs, termed the PTAP motif (for example, from HIV-1), interacts with the TSG101 protein that becomes recruited as part of the ESCRT complexes. Another of these L-domain motifs, termed PPPY motif (also referred to as the "PY motif" or the "PY L-domain motif;" for example, from ASLV), interacts with the Nedd4 family of proteins that is also recruited by ESCRT-II-associated proteins or AIP1. While it is often the case that certain viruses have a viral protein might encode both types of L-domains, typically only one predominates in the viral budding process through interactions with ESCRT machinery. The inventors have devised novel, robust screening methods to identify compounds that interfere with the interaction between viral L-domains that include the PPPY motif or PTAP motif and ESCRT component, TSG101 or ESCRT-linked component, Nedd4 family proteins. These screening methods enable one to rapidly identify compounds that inhibit the interactions of both Nedd4 and TSG101 with the viral L-domain motifs, thereby providing a high-throughput strategy to obtain candidate lead compounds having utility as novel antiviral agents for inhibiting virus budding and release from infected cells.

Some candidate lead compounds can display potency at inhibiting only Nedd4-mediated ESCRT pathways or TSG101-mediated ESCRT pathways, thereby offering specific antiviral activity for one type of virus or virus family. Yet other candidate lead compounds can display potency at inhibiting both Nedd4-mediated ESCRT pathways and TSG101-mediated ESCRT pathways, thereby offering broad-spectrum antiviral activity to a plurality of diverse enveloped virus families using a common ESCRT pathway. Thus, the screening methods disclosed herein contemplate identification of compounds having either narrow-spectrum antiviral effects or broad-spectrum antiviral effects. Methods for identifying compounds that inhibit Nedd4-mediated ESCRT pathways and TSG101-mediated ESCRT pathways have been described. (See U.S. Publication Nos. 2014/0179637 and 2017/0095485, the contents of which are incorporated herein by reference in their entireties).

The compounds utilized in the treatment methods disclosed herein may exhibit one or more biological activities. The disclosed compounds may function to inhibit the release of enveloped viruses from infected cells. In some embodiments, the disclosed compounds inhibit release of enveloped viruses from infected cells by at least 50%, 60%, 70%, 80%, 90%, 95%, 96%, 97%, 98%, or 99% at a concentration of less than about 100 $\mu$M, 50 $\mu$M, 10 $\mu$M, 1 $\mu$M, 0.1 $\mu$M, 0.05 $\mu$M, 0.01 $\mu$M, 0.005 $\mu$M, 0.001 $\mu$M, or less, relative to a control. Preferably, the disclosed compounds are not toxic and/or do not inhibit the growth of cells (preferably by not more than 50%, 40%, 30%, 20%, 10%, 5%, 4%, 3%, 2% or less) at a concentration of greater than about 0.001 $\mu$M, 0.005 $\mu$M, 0.01 $\mu$M, 0.5 $\mu$M, 0.1 $\mu$M, 1.0 $\mu$M, 10 $\mu$M, and 100 $\mu$M or higher. Concentration ranges of the disclosed compounds for use in the disclosed methods also are contemplated herein, for example, a concentration range bounded by end-point concentrations selected from 0.001 $\mu$M, 0.005 $\mu$M, 0.01 $\mu$M, 0.5 $\mu$M, 0.1 $\mu$M, 1.0 $\mu$M, 10 $\mu$M, and 100 $\mu$M.

The compound utilized in the treatment methods disclosed herein may bind to one or more cellular proteins in order to inhibit viral release from infected cells. In some embodiments, the compounds utilized in the disclosed treatment methods may bind covalently to the one or more cellular proteins (e.g. TSG101).

FTS Assay for Detecting Direct Binding Interactions Between Test Compounds and ESCRT Component Proteins The compound utilized in the treatment methods disclosed herein may bind to one or more cellular proteins in order to inhibit viral release from infected cells. In some embodiments, the compounds utilized in the disclosed treatment methods may bind covalently and/or non-covalently to the one or more cellular ESCRT component proteins (e.g. TSG101 and/or Nedd4 proteins). Methods for detecting direct binding interaction between test compounds and ESCRT component proteins have been described and include fluorescence-based thermal shift (FTS) assays. (See U.S. Publication Nos. 2014/0179637 and 2017/0095485, the contents of which are incorporated herein by reference in their entireties).

The fluorescence-based thermal shift assay is based on the observation that a protein unfolds upon heating, exposing the hydrophobic residues within its tertiary structure. The unfolding temperature (Tm) is determined by the protein's primary sequence and solution environment. The FTS assay uses a fluorescent dye sensitive to a hydrophobic environment to probe protein stability and its modulation by small molecule ligands. The dye has a low fluorescence quantum yield when in a polar environment. Once in contact with the hydrophobic core normally buried within a folded protein that has become exposed during the thermal unfolding (melting) process, the quantum yield of the dye increases, thus providing a reporting signal. Furthermore, a protein's stability can be affected by ligand binding, resulting in an increase or decrease in its melting temperature. FTS assay uses the Tm shift upon binding of a ligand to identify hit compounds for drug discovery.

In Vivo Screening Methods-Based Molecular Genetic Assays, Cell-Based VLP Production Assays and Whole-Virus Replication Assays Candidate compounds having an inhibitory effect of fluorescence have also been evaluated for their ability to interfere with normal cellular physiology and growth by, for example, determining cytotoxicity profiles of the compounds as a function of dose response and incubation time with the cells. One advantage of the in vivo assay is that it provides additional opportunities to survey test compounds that otherwise might not be possible with the aforementioned biochemical assays (for example, with assays involving certain ESCRT component polypeptides having limited solubility in vitro). Other further advantages of in vivo assays of this sort is that they can provide a useful model for studying compound transport and clearance in cells as would be important for determining ADME profiles (for examples, bioactivity, bioavailability, bio-inactivation, among others) at a cellular level, as well as provide additional confirmatory evidence of the biological potency of the compounds in a more meaningful, biological context.

For candidate lead compounds identified through one or more of the aforementioned screening methods, biological assays have been established to evaluate the specific antiviral inhibitory effects the compounds have on virus budding and release. In one assay, virus like particle ("VLP") production can be evaluated as a function of test compound dose. Follow-up experiments well within the skilled artisan's grasp include evaluating other aspects of viral replication, as monitored by standard biochemical assays (PCR, RT-PCR, western blot methods and the like) as well as cell toxicity effects. These assays and other aspects are described in detail in the Examples or are otherwise well understood in the art. VLP production assays have provided evidence of candidate lead compounds showing antiviral inhibitory effect on virus particle release as a function of dose, experiments then can proceed to demonstrate the antiviral effect in whole virus replication assays.

The aforementioned in vivo and in vitro screening methods can be combined either in series or in parallel (and in any order) to identify compounds having either narrow-spectrum activity against a few viruses or broad-spectrum antiviral activity against many different viruses. In this manner, different antiviral compounds can be discerned having discrete types of inhibitory activity. Further, one can identify gradients of antiviral potency across entire classes of viruses by evaluating the dose response profiles in a combination of biochemical and biological assays with different virus families having different viral L-domain motifs, as described herein. Moreover, combinations of compounds have TSG101-specific inhibitory activity and Nedd4 family-specific inhibitory activity can be tested against virus infection to determine whether the drug combinations block virus access to the ESCRT-complex dependent pathways are blocked for enveloped virus release.

These approaches have clear utility for two simple reasons. First, L-domains encoding the aforementioned PY motifs and PTAP motifs can be found with viral proteins for single virus families. Thus, viruses having both types of L-domains can potentially utilize both pathways mediated by Nedd 4 and TSG101. Second, the L-domains used by viruses are interchangeable. Thus, there is a need for compounds to disrupt both interactions between viral L-domains with the two different pathways mediated by Nedd 4 and TSG101, wherein virus budding and release can occur from different cellular membranes.

The identified compound inhibitors have utility as antiviral therapeutic agents. The therapy is a post infection treatment that will slow down the spread of virus by preventing particles from releasing from infected cell surfaces. The accumulation of particles will enhance detection by the immune system, which will clear the infection. The human body already has an innate immunity response that targets the release of virus particles late in infection. Thus, the above approach has viability because it will complement the natural immunity mechanism.

Pharmaceutical Compositions

The disclosed compounds may be formulated as therapeutics for treating viral infections and diseases associated with viral infections. The compounds utilized in the methods disclosed herein may be formulated as pharmaceutical compositions that include: (a) a therapeutically effective amount of one or more compounds as disclosed herein; and (b) one or more pharmaceutically acceptable carriers, excipients, or diluents. The pharmaceutical composition may include the compound in a range of about 0.1 to 2000 mg (preferably about 0.5 to 500 mg, and more preferably about 1 to 100 mg). The pharmaceutical composition may be administered to provide the compound at a daily dose of about 0.1 to about 1000 mg/kg body weight (preferably about 0.5 to about 500 mg/kg body weight, more preferably about 50 to about 100 mg/kg body weight). In some embodiments, after the pharmaceutical composition is administered to a subject (e.g., after about 1, 2, 3, 4, 5, or 6 hours post-administration), the concentration of the compound at the site of action may be within a concentration range bounded by end-points selected from 0.001 μM, 0.005 μM, 0.01 μM, 0.5 μM, 0.1 μM, 1.0 μM, 10 μM, and 100 μM (e.g., 0.1 μM-1.0 μM).

In some embodiments of the disclosed treatment methods, the subject may be administered a dose of a compound as low as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg once daily, twice daily, three times daily, four times daily, once weekly, twice weekly, or three times per week in order to treat the disease or disorder in the subject. In some embodiments, the subject may be administered a dose of a compound as high as 1.25 mg, 2.5 mg, 5 mg, 7.5 mg, 10 mg, 12.5 mg, 15 mg, 17.5 mg, 20 mg, 22.5 mg, 25 mg, 27.5 mg, 30 mg, 32.5 mg, 35 mg, 37.5 mg, 40 mg, 42.5 mg, 45 mg, 47.5 mg, 50 mg, 52.5 mg, 55 mg, 57.5 mg, 60 mg, 62.5 mg, 65 mg, 67.5 mg, 70 mg, 72.5 mg, 75 mg, 77.5 mg, 80 mg, 82.5 mg, 85 mg, 87.5 mg, 90 mg, 100 mg, 200 mg, 500 mg, 1000 mg, or 2000 mg, once daily, twice daily, three times daily, four times daily, once weekly, twice weekly, or three times per week in order to treat the disease or disorder in the subject. Minimal and/or maximal doses of the compounds may include doses falling within dose ranges having as end-points any of these disclosed doses (e.g., 2.5 mg-200 mg).

In some embodiments, a minimal dose level of a compound for achieving therapy in the disclosed methods of treatment may be at least about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. In some embodiments, a maximal dose level of a compound for achieving therapy in the disclosed methods of treatment may not exceed about 10, 20, 30, 40, 50, 60, 70, 80, 90, 100, 150, 200, 250, 300, 350, 400, 450, 500, 550, 600, 650, 700, 750, 800, 850, 900, 950, 1000, 1200, 1400, 1600, 1800, 1900, 2000, 3000, 4000, 5000, 6000, 7000, 8000, 9000, 10000, 15000, or 20000 ng/kg body weight of the subject. Minimal and/or maximal dose levels of the compounds for achieving therapy in the disclosed methods of treatment may include dose levels falling within ranges having as end-points any of these disclosed dose levels (e.g., 500-2000 ng/kg body weight of the subject).

The compounds utilized in the methods disclosed herein may be formulated as a pharmaceutical composition in solid dosage form, although any pharmaceutically acceptable dosage form can be utilized. Exemplary solid dosage forms include, but are not limited to, tablets, capsules, sachets, lozenges, powders, pills, or granules, and the solid dosage form can be, for example, a fast melt dosage form, controlled release dosage form, lyophilized dosage form, delayed release dosage form, extended release dosage form, pulsatile release dosage form, mixed immediate release and controlled release dosage form, or a combination thereof.

The disclosed compounds or pharmaceutical compositions comprising the disclosed compounds may be administered in methods of treatment. For example, the disclosed compounds or pharmaceutical compositions comprising the disclosed compounds may be administered in methods of treating viral infections and/or the symptoms thereof.

Optionally, the disclosed compounds or pharmaceutical compositions comprising the disclosed compounds may be administered with additional therapeutic agents, optionally in combination, in order to treat viral infections. In some embodiments of the disclosed methods, one or more additional therapeutic agents are administered with the disclosed compounds or with pharmaceutical compositions comprising the disclosed compounds, where the additional therapeutic agent is administered prior to, concurrently with, or after administering the disclosed compounds or the pharmaceutical compositions comprising the disclosed compounds. In some embodiments, the disclosed pharmaceutical composition are formulated to comprise the disclosed compounds and further to comprise one or more additional therapeutic agents, for example, one or more additional therapeutic agents for treating viral infections.

Ilaprazole for Inhibiting Release of Enveloped Viruses from Infected Cells

Disclosed are methods for treating an infection by an enveloped virus in a patient in need thereof. The methods include administering to the patient a compound that inhibits or blocks release of the enveloped virus from an infected cell. As such, the disclosed methods include methods of inhibiting or blocking release of an enveloped virus from a cell.

In some embodiments, the disclosed methods comprise administering to the patient a prazole-type compound having a substituted (pyridin-2-yl)methylsulfinyl-benzimidazole core. Suitable prazole-type compounds may include a compound of a formula:

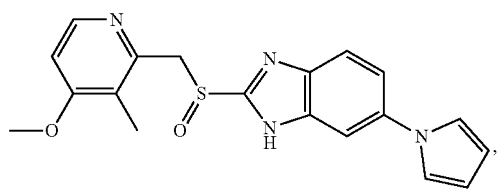 [SMILES: COc1ccnc(CS(=O)c2nc3ccc(-n4cccc4)cc3[nH]2)c1C]

, which otherwise is referred to as 2-[(4-methoxy-3-methylpyridin-2-yl)methylsulfinyl]-6-pyrrol-1-yl-1H-benzimidazole or Ilaprazole.

The disclosed methods may be performed in order treat infection by an enveloped virus in a patient in need thereof, for example, by inhibiting or blocking release of an enveloped virus in infected cells using this common mechanism. Suitable enveloped viruses for the disclosed methods may include, but are not limited to Lassa fever virus, lymphocytic choriomeningitis virus, Ebola virus, Marburg virus, hepatitis B virus, herpes simplex virus type 1, herpes simplex virus type 2, cytomegalovirus, simian virus type 5, mumps virus, avian sarcoma leucosis virus, human immunodeficiency virus type 1, human T-lymphotrophic virus type 1, equine infectious anemia virus, vesicular stomatitis virus, rabies virus, coronavirus, and combinations thereof.

In some embodiments, the disclosed methods may be performed in order treat infection by coronavirus in a patient in need thereof, for example, by administering a proton pump inhibitor to the patient. Coronaviruses are known in the art and may include human coronavirus, including the human coronavirus that cause sudden acute respiratory syndrome (SARS), middle east respiratory syndrome (MERS), and coronavirus virus disease 19 (COVID-19). Coronaviruses make up the subfamily Orthocoronavirinae, in the family Coronaviridae, order Nidovirales, and realm Riboviria. Coronaviruses are enveloped viruses with a positive-sense single-stranded RNA genome and a nucleocapsid of helical symmetry. The genome size of coronaviruses ranges from approximately 26 to 32 kilobases, which is one of the largest among genome sizes amongst RNA viruses. Coronaviruses have characteristic club-shaped spike proteins (S) that project from their surface, which in electron micrographs create an image reminiscent of the solar corona, and hence their name.

Coronaviruses suitable for treatment by the disclosed methods may include, but are not limited to Human coronavirus 2229E, Human coronavirus NL63, Human coronavirus HKU1, Miniopterus bat coronavirus 1, Miniopterus bat coronavirus HKU8, Porcine epidemic diarrhea virus, Rhinolophus bat coronavirus HKU2, Scotophilus bat coronavirus 512. Betacoronavirus 1 (Bovine Coronavirus, Human coronavirus OC43), Human coronavirus HKU1, Murine coronavirus, *Pipistrellus* bat coronavirus HKU5, *Rousettus* bat coronavirus HKU9, Severe acute respiratory syndrome-related coronavirus (SARS-CoV, SARS-CoV-2), *Tylonycteris* bat coronavirus HKU4, Middle East respiratory syndrome-related coronavirus, Hedgehog coronavirus 1 (EriCoV), Beluga whale coronavirus SW1, Infectious bronchitis virus, Bulbul coronavirus HKU11, and Porcine coronavirus HKU15. In particular, the disclosed methods may be practiced in order to treat infection with severe acute respiratory syndrome coronavirus 2 (SARS-CoV-2), which is the virus strain that causes coronavirus disease 2019 (COVID-19), a respiratory illness. SARS-CoV-2 utilizes the human angiotensin converting enzyme 2 cell surface protein to bind and target cells for infection via the spike protein (S).

In the disclosed methods, the disclosed compound have antiviral activity against an enveloped virus. In some embodiments, the disclosed compounds have antiviral activity against an enveloped virus selected from (i) inhibiting formation of an associative complex, (ii) disrupting formation of an associative complex, and (iii) both of (i) and (ii), optionally wherein the associative complex comprises an L-domain motif of the enveloped virus and at least one cellular polypeptide, or fragment thereof, capable of binding the L-domain motif of the enveloped virus. Preferably, the L-domain motif comprises at least one of a PY-motif and/or a PTAP-motif. Optionally, the L-domain motif comprises at least one amino acid sequence selected from the group consisting of SEQ ID NOS: 1-22 of U.S. Published Application No. 2019-0209589 (SEQ ID NOS 1-22), the content of which is incorporated herein by reference in its entirety. Preferably, the at least one cellular polypeptide comprises an ESCRT complex protein. Optionally, the ESCRT complex protein comprises at least one member selected from a Nedd 4-related family peptide or a fragment thereof, TSG101 or a fragment thereof, and combinations thereof. Optionally, the ESCRT component protein comprises at least one amino acid sequence selected from the group consisting of SEQ ID NOS: 24, 29, 32, and 33 of U.S. Published Application No. 2019-0209589 (SEQ ID NOS 23-26), the content of which is incorporated herein by reference in its entirety. The informal sequence listing that accompanies this application forms part of the description of the invention.

EXAMPLES

The following Example is illustrative and is not intended to limit the claimed subject matter.

Reference is made to Leis J. et al., "Ilaprazole and other novel prazole-based compounds that bind Tsg101 and inhibit viral budding of HSV-1/2 and HIV from cells," J. Virol. 2021 Mar. 17; 1-20, the content of which is incorporated herein by reference it its entirety.

Title—Ilaprazole and Other Novel Prazole-Based Compounds that Bind Tsg101 Inhibit Viral Budding of HSV-1/2 and HIV from Cells Abstract In many enveloped virus families, including HIV and HSV, a crucial, yet unexploited, step in the viral life cycle is releasing particles from the infected cell membranes. This release process is mediated by host ESCRT complex proteins, which are recruited by viral structural proteins and provides the mechanical means for membrane scission and subsequent viral budding. The prazole drug, tenatoprazole, was previously shown to bind to ESCRT complex member Tsg101 and to quantitatively block the release of infectious HIV-1 from cells in culture. In this report we show that tenatoprazole and a related prazole drug, ilaprazole, effectively block infectious Herpes Simplex Virus (HSV)-1/2 release from Vero cells in culture. By electron microscopy, we found that both prazole drugs block the transit of HSV particles through the cell nuclear membrane resulting in their accumulation in the nucleus. Ilaprazole also quantitatively blocks the release of HIV-1 from 293T cells with an EC50 of 0.8-1.2 µM, which is much more potent than tenatoprazole. Our results indicate that prazole-based compounds may represent a class of drugs with potential to be broad-spectrum antiviral agents against multiple enveloped viruses, by interrupting cellular Tsg101 interaction with maturing virus, thus blocking the budding process that releases particles from the cell.

Importance

These results provide the basis for the development of drugs that target enveloped virus budding that can be used ultimately to control multiple virus infections in humans.

INTRODUCTION

The advent of antibiotics had a major impact on controlling bacterial infections in patients worldwide, with a single drug being used to treat multiple infections. Unfortunately, antivirals have not had the same success. There are many contributing factors to this shortcoming, foremost the fact that few mechanisms are shared by different viruses, which limits targets for a broad-spectrum antiviral. Consequently, approved antivirals generally act against individual rather than groups of viruses, limiting a single drug's potential.

Enveloped viruses bud from the host cell membranes and use the acquired lipid layer as a protective coat that also contains the glycoproteins required for infection of other cells. Enveloped viruses do not encode the machinery needed for budding and must recruit host-cell proteins to bud from cells. In HIV, ESCRT proteins are recruited to virus budding complexes through an interaction between the L-domain (PT\SAP motif) in virus structural proteins (3-7) with cellular protein Tsg101 (Tumor susceptibility gene 101), a homolog of the E2 ubiquitin conjugating enzyme and a member of the ESCRT-I complex (6, 8-11). Tsg101 recruits the cellular ESCRT-III complex, which provides the mechanical means for viruses to passage through cell membranes to be released from cells (10, 12-19). In contrast to HIV, herpes simplex virus (HSV) assembles particles in the nucleus and must passage through the nuclear membrane into the cytoplasm where it exchanges membranes to become infectious and then is released from the cell membrane. The ESCRT proteins are required for this passage (20, 21, 29). Thus, virus budding may present a common target for treating multiple virus infections.

In support of targeting this pathway, a recent seminal discovery in our lab established that an interferon-induced protein, Interferon Stimulated Gene 15 (ISG15), specifically targets the ESCRT-III proteins in budding complexes to block the release of viruses (1, 22-24). This indicates that the human immune system evolved to target the ESCRT pathway to control viral infections and supports that this is a natural target. Another group identified single-nucleotide polymorphic sites in the 5' region of Tsg101, located at positions −183 and +181 relative to the translation start signal, which affect the rate of AIDS progression among Caucasians (25). These data support the hypothesis that variation in Tsg101 affects efficiency of Tsg101-mediated release of viral particles from infected cells, altering plasma viral load levels and subsequent disease progression. Taken together, these investigations indicate that Tsg101 and ESCRT proteins present a natural antiviral target.

Currently the prazole family of drugs is best known for their role as proton pump inhibitors (PPIs) and a few, namely omeprazole (Prilosec), esomeprazole (Nexium) and ilaprazole (Adiza, Noltec, Yi Li An), are marketed to control symptoms of gastroesophageal reflux disease (GERD) in either the US or abroad. PPIs form a covalent bond with the active site of proton pumps, inhibiting their ability to acidify the stomach and reducing symptoms associated with over-acidification (26). Recent reports indicate that drugs from the prazole family, including tenatoprazole and esomeprazole, form a disulfide linkage to Tsg101, which results in blocking the release of HIV-1 from cells in culture (5).

In the present manuscript, we demonstrate that multiple prazole drugs block the budding of HSV-1 and HSV-2 from Vero cells in culture, strengthening the case for the broad-spectrum potential of this mechanism/drugs. Most notably, we identified one prazole drug, ilaprazole, which blocks the release of both HIV-1 and HSV-1/2 from cells at an efficiency more potent than reported for tenatoprazole. Ilaprazole acts in the low µM range without detectable cell toxicity at inhibitory concentrations. To further define the mechanism of action of these prazole drugs on HSV infections, we identified the site of blockage of herpesvirus release, which appears to be different from HIV-1. While the blockage to HIV-1 particle release is at the outer cell membrane (5), the prazole drugs appear to first block the passage of the herpesvirus through the nuclear membrane. This prevents particles being released into the cytosol, where maturation of their envelope membrane occurs to produce infectious virus and where they bud from the cell. With the prazole-based inhibitors being effective in both HIV and HSV, targeting Tsg101 could lead to a broad-spectrum antiviral therapy.

Results

Identification of prazole compounds that bind the UEV ubiquitin-binding domain of Tsg101. We screened chemical compounds using a fluorescence thermal shift (FTS) assay (27, 28) to identify small molecules that bind directly to a truncated form of Tsg101 (amino acids 1-145) which contains the Ubiquitin E2 variant (UEV) ubiquitin-binding domain (FIG. 1). The UEV, which contains the PT/SAP binding domain in addition to the ubiquitin-binding domain, provides chaperone functions to HIV-1 Gag that is independent of its interaction with the PS/TAP motif, and contains the prazole binding site (5). This truncated Tsg101, called Tsg101-UEV, was used because full-length Tsg101 has significant solubility issues in aqueous solution. Tsg101 is an adaptor protein and thus lacks a readily deployable functional assay, making FTS a tractable approach to identify interacting compounds. FTS monitors protein thermal denaturation using SYPRO-Orange, a dye which fluoresces when bound to hydrophobic surfaces, which allows monitoring of the changes in hydrophobic surface exposure during protein denaturation (27). Since ligand binding affects protein thermal stability, it can be detected through modulation of protein thermal denaturation (melting) as a shift in melting temperature (Tm). Tsg101-UEV has a well-defined melting curve suitable for FTS. We used the FTS assay to identify compounds that bind to Tsg101-UEV.

We compared thermal denaturation profile for Tsg101-UEV in the presence and absence of tenatoprazole and found that it destabilizes the native protein structure, indicating that it binds Tsg101-UEV (FIG. 1A). We also tested tenatoprazole against proteins unrelated to Tsg101, including DHPH, ENO1, MEK4, and did not observe a Tm shift, indicating that the Tm shift of Tsg101-UEV was due to specific interaction of the prazole compound (FIG. 1B). This specific binding is consistent with a previous NMR structure in which tenatoprazole forms a covalent disulfide bond to Cys73 in the UEV domain of the protein (5). This disulfide bond formation can be prevented by including the reducing agent DTT in the assay (FIG. 1C). The addition of DTT abolished the Tsg101-UEV Tm shift caused by the prazoles. Therefore, the addition of DTT to the FTS assay is a facile means to ascertain if prazole analogs interact with Tsg101-UEV in a covalent manner.

Tenatoprazole inhibits herpesvirus release from Vero cells. Tenatoprazole and esomeprazole were shown to quantitatively inhibit the release of infectious HIV-1 from 293T cells in culture, and it was suggested that these effects may be mediated via changes in viral interaction with Tsg101, a key component of the cellular ESCRT complex (5, 29). Given multiple reports suggesting that herpesviruses also use cellular ESCRT proteins in their replication process (20, 21) we tested if the Tsg101-binding prazole drugs, which blocked budding of HIV-1, would also block the release of herpesviruses from cells.

We infected Vero cells with HSV-1 and HSV-2 for two hours at a multiplicity of infection (MOI in pfu\cell) of 0.1 to assay the antiviral activity of tenatoprazole. Following infection, cells were treated with different concentrations of tenatoprazole. After 24 or 48 h the media fractions were collected and released virus titers were determined by standard plaque assays (30). Tenatoprazole caused a 3-log drop of HSV-1 and 4-5 log drop of HSV-2 in released infectious virus from Vero cells at 24 hours after infection in a dose dependent manner (Table 1, shown in FIG. 5, columns 2 and 3) with calculated EC50's ranging from 48-80 µM. Similar results were obtained at 48 h after infection (Table 1, shown in FIG. 5, columns 5 and 6). Total virus titer was also determined to differentiate between virus released into the media and infectious particles present in cell lysate. Total infectious virus particles were reduced by tenatoprazole, but not as strongly as virus released into the media (Table 1, shown in FIG. 5, compare columns 3 and 4). The concentrations of tenatoprazole that blocked virus release were nontoxic to Vero cells as determined by a 96® AQueous One Solution cell proliferation assay reagent (Table 1, shown in FIG. 5, column 7). Taken together, tenatoprazole inhibited levels of both released and infectious virus particles without affecting cell viability at effective concentrations.

Figure 2:
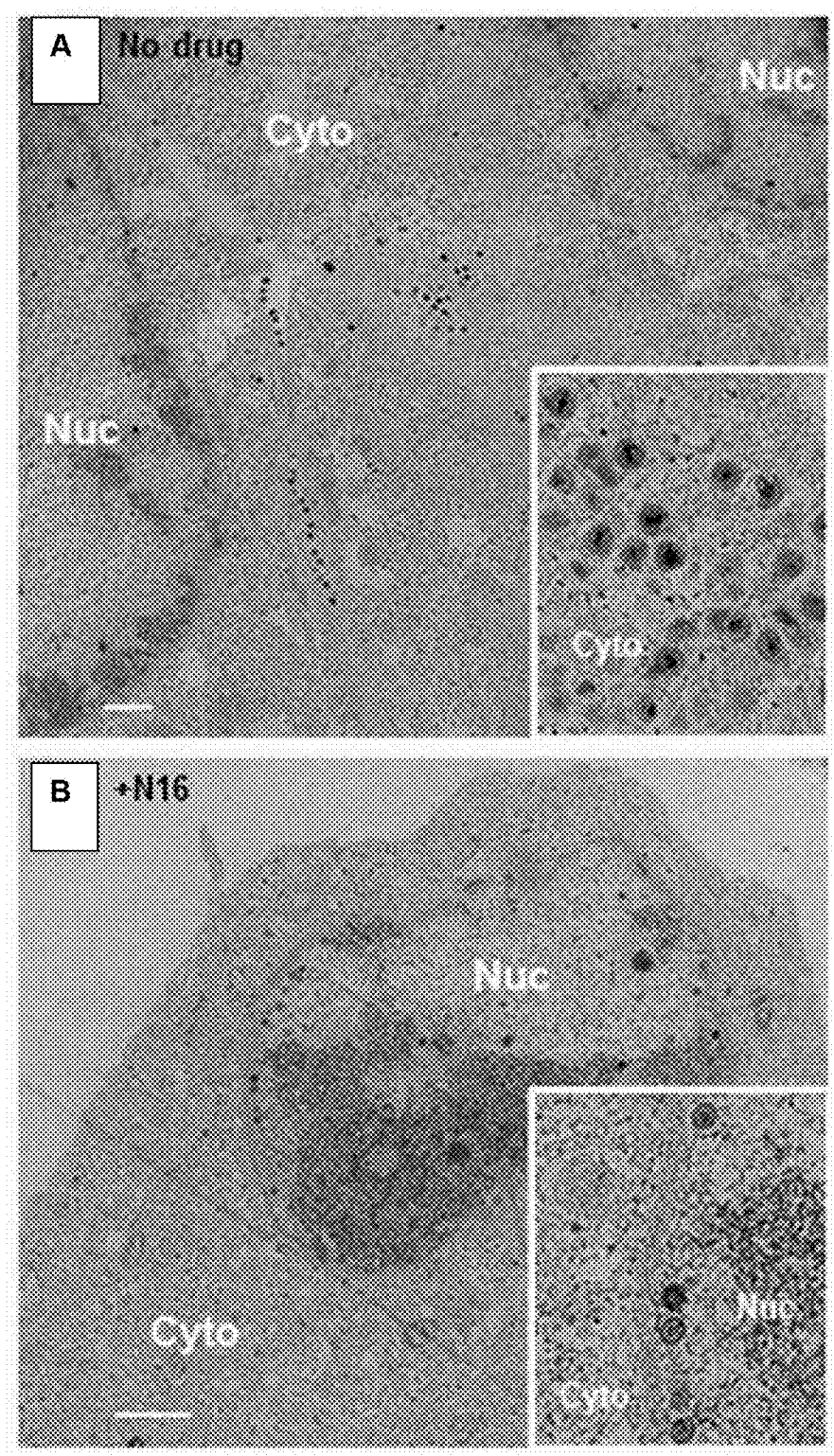
FIG. 2 Inhibitory effect of tenatoprazole on HSV-2 production and location of virus particles inside of infected cells. Cells with virus were untreated (A) or treated with 105 µM tenatoprazole (N16) (B) for 24 h and examined by transmission electron microscopy. In each case, 80 cells where virus particles were observed were examined. For untreated cells, we observed an average of 120 particles in the cytoplasm ranging from 28 to 204 particles. In the nucleus, we observed an average of 16 particles ranging from 10 to 22 particles. In the presence of drug, we observed a significant increase in dense material in the nucleus with some particles associated with it. We observed an average of 31 particles, ranging from 8 to 48. In the cytoplasm, we did not detect virus particles. Bar=1 µm. Inset, higher magnification image.

Cellular location of tenatoprazole inhibition. We next imaged herpesvirus infected-Vero cells using transmission electron microscopy to determine the site of inhibition of release of virus and whether it was similar to observations of HIV-1 release from 293T cells. Vero cells grown on glass cover slips were infected with HSV-2 at MOI of 0.1 pfu/cell for 2 h and then treated for 24 h with 105 µM tenatoprazole or vehicle control. Using electron microscopy, we examined eighty cells with virus particles, and representative images are shown in FIG. 2. In the no drug control, virus particles were in both the nucleus and cytoplasm near the cell surface (FIG. 2A). In the tenatoprazole-treated cells the cytosol of all of the intact cells was largely devoid of virus particles (FIG. 2B). Instead, we observed large pockets of granular material accumulated in the nucleus and immature virus particles inside the nucleus and lining the inside of the nuclear membrane (inset, B). This result suggests that tenatoprazole blocks the passage of herpesvirus particles through the nuclear membrane, in contrast to the report of Pawliczek and Crump (31). This result also differs from that observed with HIV-1. Because tenatoprazole binds Tsg101, it suggests that the ESCRT-I protein complex is involved in transport of HSV-2 through the nuclear membrane and/or particle assembly.

Identification of potent prazole-based inhibitors. Despite the lack of cell toxicity signal at effective tenatoprazole concentrations, the effective concentration is too high for use as a clinical therapy. Therefore, more potent analogs are required to explore antiviral therapeutic potential. We set out to identify and test other analogs which were more potent prazole analogs. We began by searching PubChem for analogs of tenatoprazole. We identified and obtained a dozen such compounds from commercial sources and prioritized these for testing based on structural similarities around the sites where tenatoprazole covalently linked to Cys73 of Tsg101. To this end, tenatoprazole, lansoprazole, rabeprazole, dexlansoprazole, pantoprazole, esomeprazole, 4-desmethoxy-omeprazole, omeprazole-N-oxide, omeprazole, and ilaprazole were assessed in the FTS assay for their ability to change the Tm of Tsg101-UEV as described above (data not shown).

Figure 3:
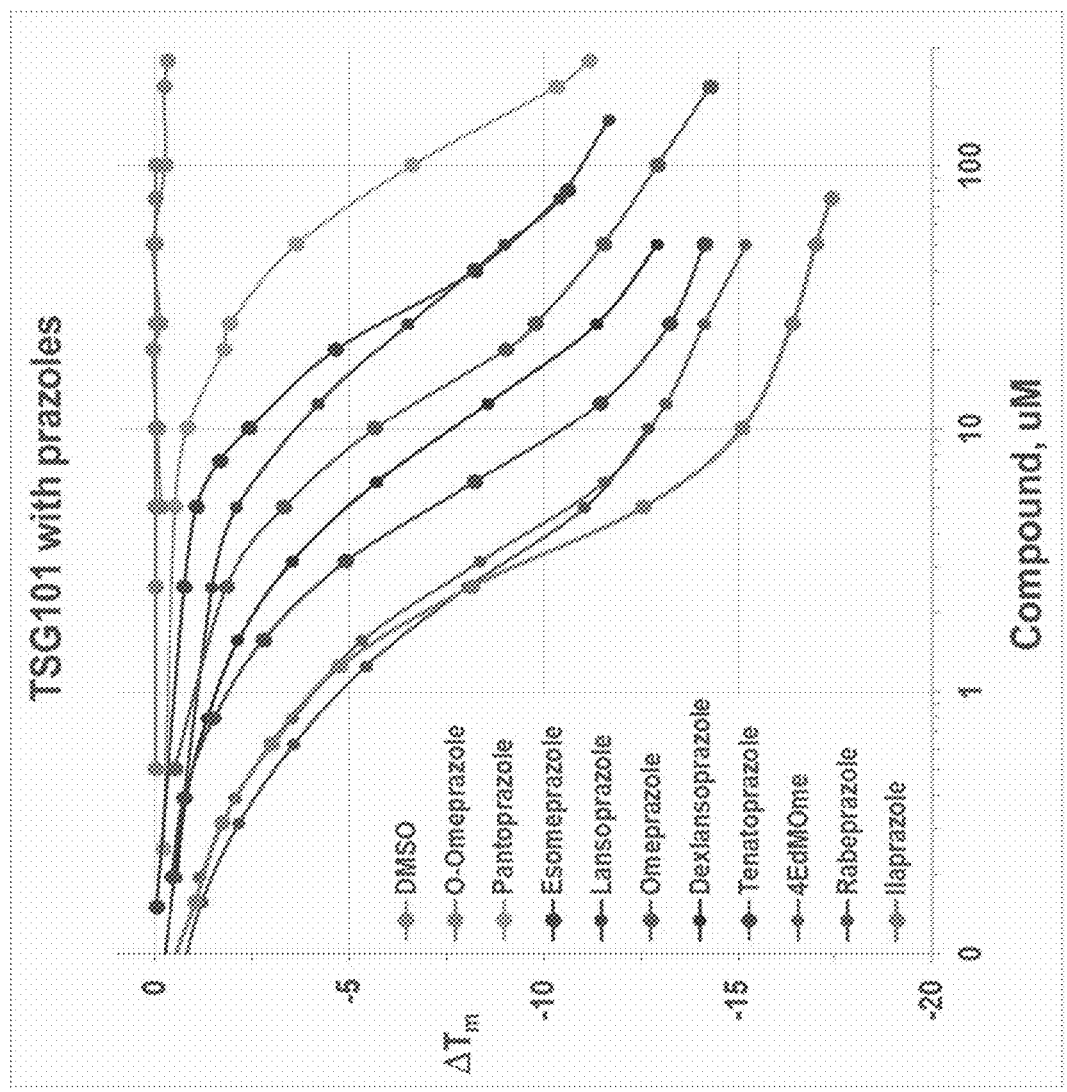
FIG. 3. Dose-response plots of Tsg101 melting temperature shift caused by 10 prazole compounds. Different concentrations of prazole compounds were incubated with Tsg101 (aa 1-145) and subjected to Fluoresecent Thermal Shift analysis as described in Materials and Methods.

We determined the dose response plots of Tsg101 melting temperature shifts caused by these prazole compounds binding to Tsg101 (1-145) (FIG. 3). Omeprazole-N-oxide is the only compound predicted not to form the covalent bond with Tsg101, since it has an oxygen linked to a ring nitrogen that is normally a hydrogen in the active prazoles (Table 2, shown in FIG. 6, right column). As expected, omeprazole-N-oxide did not cause a detectable thermal shift (FIG. 3). The smallest thermal shift was observed with pantoprazole (gray) and the largest thermal shift was observed with ilaprazole (green). Ilaprazole's ability to cause a thermal shift with Tsg101 was blocked by the addition of DTT (FIG. 1C), consistent with the idea that the compound forms a disulfide linkage to Tsg101.

Figure 6:
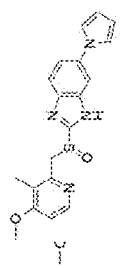
FIG. 6. Table 2. Effect of commercial prazole analogs to inhibit the release of HSV-2 from Vero cells. Different concentrations of the listed prazole drugs were incubated with HSV-2 infected Vero cells for 24 hours and then virus released into the media was quantified by plaque assays. Data presented includes the EC50 value (concentration at which virus release is inhibited by 50%). Methods are as described in the legend of Table 1.

Next, we tested the anti-herpesvirus activity of these prazole compounds (Table 2, shown in FIG. 6). To examine the effects of the compounds on the release of HSV-2 from Vero cells, we infected the cells with virus two hours prior to treatment with media containing different concentrations of compound. We incubated the cells for 24 or 48 hours and then collected the cell media fractions. Several of the analogs were inactive, including omeprazole-N-oxide, pantoprazole, and rabeprazole. We identified a number of active compounds, in which there was a 10-fold spread of inhibition activity against HSV-2, ranging from an EC50 of 140 µM (for esomeprazole) to 3-9 µM (for ilaprazole). Thus, we identified prazole analogs that are more potent than tenatoprazole.

We provide the structures of prazole compounds tested in this analysis (Table 2, shown in FIG. 6, column 3). Of note, ilaprazole contains an additional ring structure compared to tenatoprazole that is predicted to lie in a solvent exposed area of the Tsg101 structure that may serve to strengthen the interaction with Tsg101. In examining the thermal shift capacity of the prazoles, we found that the larger the thermal shift the more potent antiviral activity associated with the compound. This correlation indicates that the FTS assay is useful in evaluating structure-activity-relationships (SAR) to inform the design of new compounds (FIG. 3, FIG. 6—Table 2).

Antiviral activity of Ilaprazole on HSV-1 and HSV-2 in vitro. Based on these initial HSV-2 antiviral assay results, we selected ilaprazole for further antiviral profiling and tested it against HSV-1 (Table 3A, columns 2-5) and HSV-2 (Table 3A, columns 6-8). Ilaprazole was slightly more effective against HSV-1 than against HSV-2 with EC50 calculations ranging from 3-9 µM. These results do not indicate if the observed lower EC50 against HSV-1 compared to HSV-2 is significant or reflects differences between different viral isolates, since the two herpesviruses can be distinguished by sequence analysis and both types can cause oral and genital lesions. Ilaprazole's potency is an improvement over tenatoprazole, which inhibited in the high µM range (Table 1, shown in FIG. 5 & Table 3, shown in FIG. 7). Like tenatoprazole, ilaprazole caused a significant drop in total virus, again not as strong decrease as detected with virus released from cells. Additionally, ilaprazole was even more effective in inhibiting virus release at 72 h as at 24 h after a single application of the drug (72 h EC50 0.8-1.2 µM; compare FIG. 7, Table 3A, columns 2 & 4). Significant inhibition was still observed at 4 and 5 days after a single application of the drug (data not shown). The inhibition caused by tenatoprazole against either virus began to fall off after 48 h (data not shown). We also tested for toxicity in the range of effective concentrations and did not observe cell toxicity using the 96® AQueous One Solution cell proliferation assay reagent and WST-1 reagent over a 24 h period (Table 3B, shown in FIG. 7). Thus, ilaprazole is more potent and has longer lasting effects than tenatoprazole.

Figure 4:
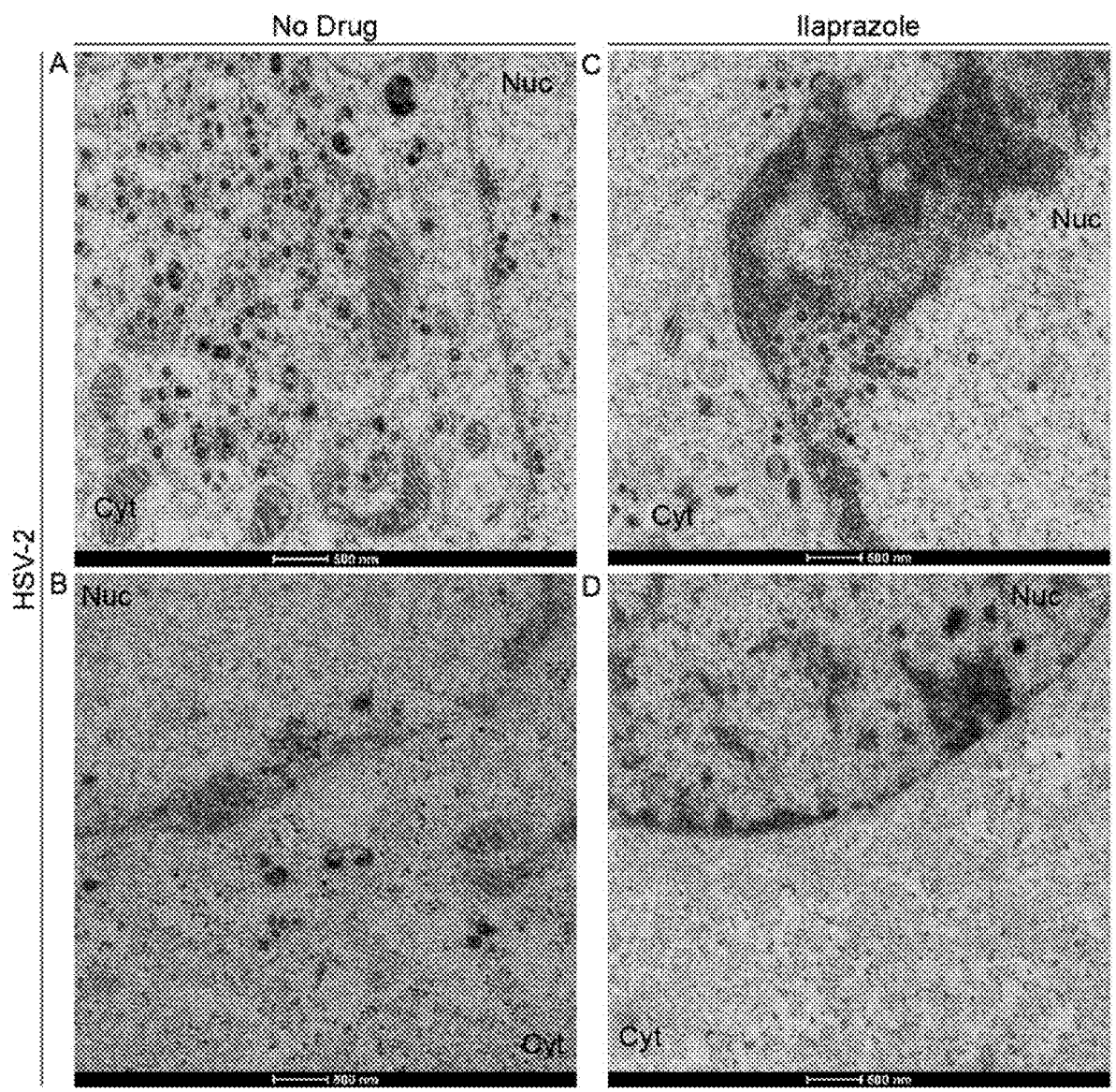
FIG. 4. Dose-response plots of Tsg101 melting temperature shift caused by 10 prazole compounds. Different concentrations of prazole compounds were incubated with Tsg101 (1-145) and subjected to Fluoresecent Thermal Sensitivity analysis as described in Materials and Methods.
Figure 4:
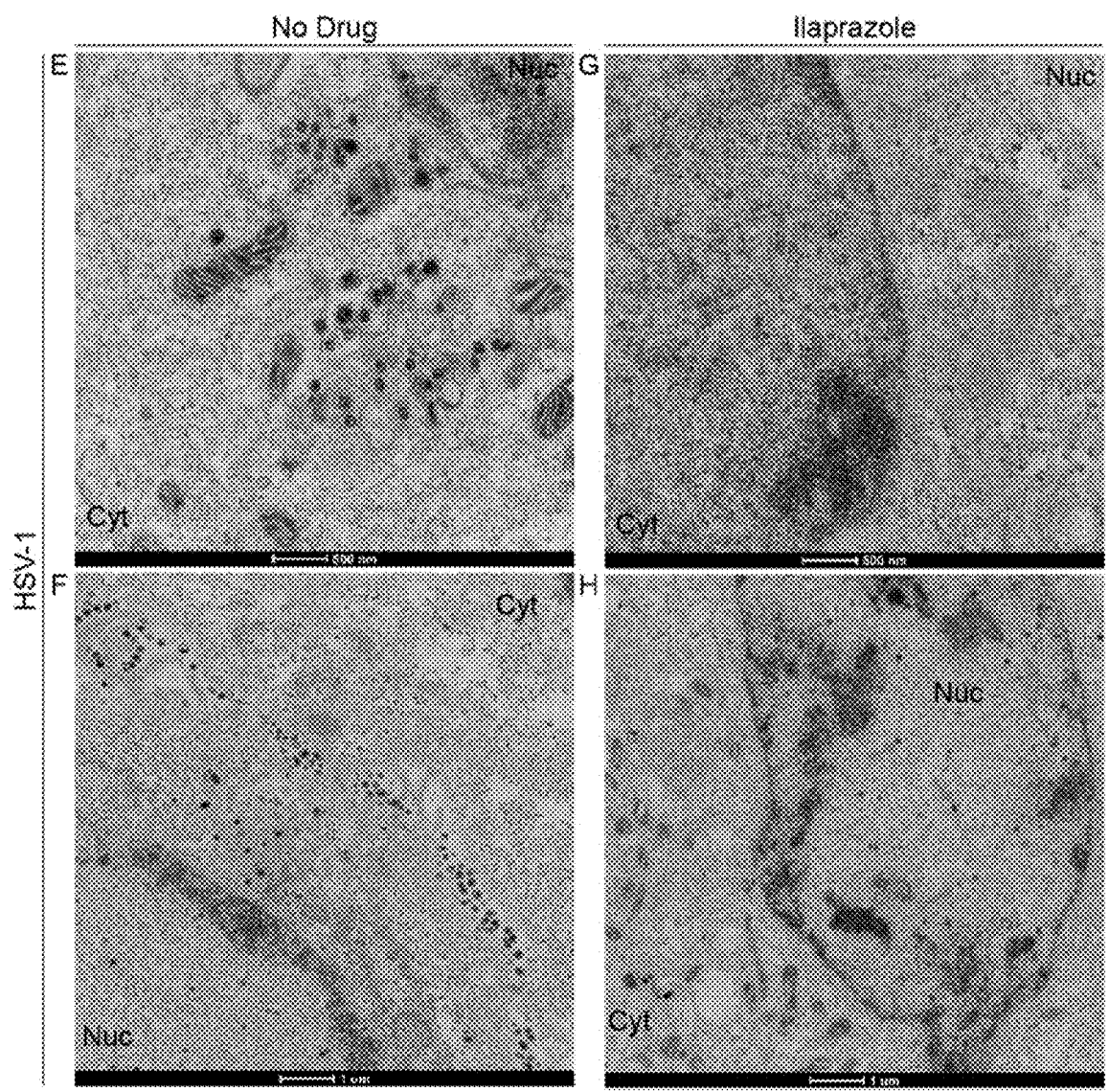

We next carried out a transmission electron microscopic examination of cells infected with HSV-2 at a MOI 0.1 in the presence and absence of 18 µM ilaprazole to determine if this drug causes the accumulation of virus particles in the nucleus of cells similar to tenatoprazole. Without drug, we observe particles in the cytoplasm and in the nucleus (FIGS. 4A & B), in the presence of drug little or no viral particles are found in the cytoplasm (FIGS. 4C & D). In both heavily infected cells (FIGS. 4A & C) and mildly infected cells (FIGS. 4B & D), treatment lead to particles being detected in the nucleus and arrayed along the nuclear membrane but lacking in the cytosol. This indicates that location of particles in the cell in the presence of drug is independent of the number of particles observed. Similar results were obtained with HSV-1 infected cells (FIG. 4E-H). Particles are seen in both the cytoplasm and nucleus in the absence of drug and just in the nucleus in the presence of drug. These results are similar to the effect of tenatoprazole on HSV-2 infected cells (FIG. 2). The lower total infectious virus detected in Table 3 (FIG. 7) is consistent with blockage of the virus passaging out of the nucleus into the cytoplasm where membranes are exchanged and virus becomes infectious.

Figure 8:
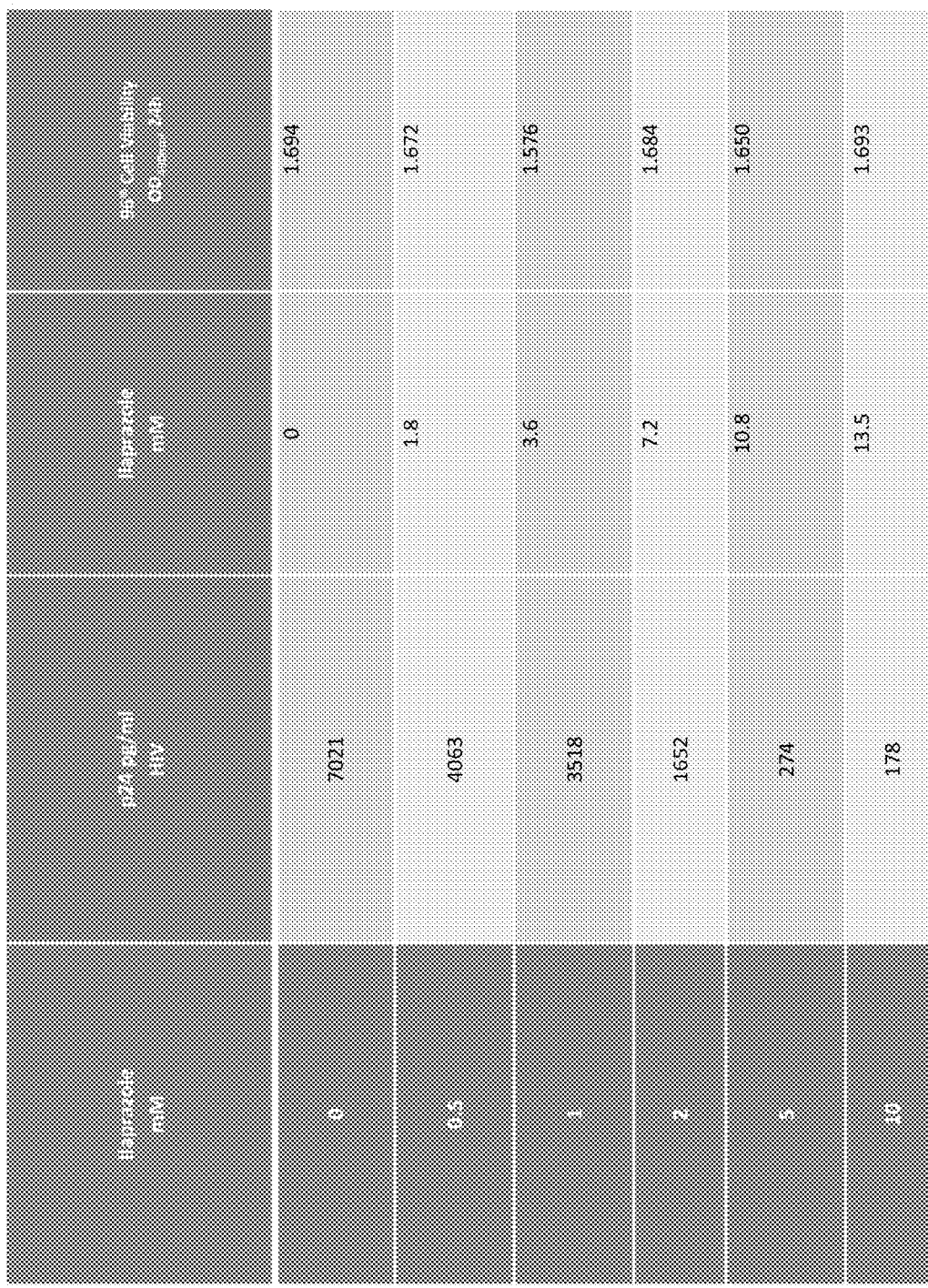
FIG. 8. Table 4. Effect of ilaprazole and novel analogs on release of HIV from 293T cells. Different concentrations of ilaprazole were incubated with HIV-1 plasmid transfected cells as described in Materials and Methods. Virus titer released into the media was determined by monitoring p24 levels 24 h post-infection using a fluorescent labeled antibody. Each experiment was repeated 4 times and the average p24 CA pg/ml presented. Cell toxicity experiments were repeated 2 times each.

Effect of Ilaprazole on release of HIV-1 in vitro. To establish the broad-spectrum potential of ilaprazole, we tested whether ilaprazole would inhibit the release of HIV-1 from 293T cells. To this end, cells were transfected with pR9-HIV-1Ba-L plasmid and release of virus into the media fraction was detected by monitoring the capsid (CA) protein (p24) via enzyme linked immunosorbent assay analysis. The drug was tested at concentrations between 0 and 40 µM and the effect of the drug on release of virus assessed (Table 4, shown in FIG. 8, column 2). Ilaprazole was effective at inhibiting the release of HIV-1 from cells with a calculated EC50 of 1 μM or less as described in Materials and Methods. We did not detect toxicity to the cells at the drug concentrations that inhibited the release of HIV-1 over the course of these experiments. Thus, ilaprazole has antiviral activity against HSV-1, HSV-2, and HIV-1, demonstrating its potential as a broad-spectrum antiviral.

DISCUSSION

We are developing a novel strategy to treat viral infections affecting humans by disrupting a common mechanism used by many enveloped viruses to bud from cells. Viral budding Inhibitors (VBI) have the potential to be broad-spectrum antiviral therapeutics, potentially being effective against herpesvirus (29, 31-35), retro/lenti- (5, 29), arena- (LFV, LCMV) (36, 37), flavi- (HCV) (38, 39), filo- (Ebola, MarV) (40-47), hepadna- (HBV) (48), some paramyxo- (SV5, MuV) (49-51) and rhabdoviruses (VSV, RV) (9, 52, 53). VBIs would require testing for antiviral activity towards these different viruses before clinical use, but nonetheless present a strong starting point for identifying therapeutics.

In this work we demonstrate antiviral activity of prazole compounds, with no detectable cell toxicity at effective concentrations, against two viruses that use different mechanisms for viral replication. Of particular note is that the viral genomes are very different, with HIV being RNA-based and HSV being DNA-based. That one compound works against viruses with such stark difference in viral life cycle types supports that these compounds have potential as a broad-spectrum antiviral agent for current and emerging viruses. This aspect gives this approach advantage over other potential broad-spectrum antivirals, such as remdesivir, which is targeted to RNA viruses, limiting its potential as a broad-spectrum antiviral (54).

Tsg101 binding to the proline-rich viral L-domains in Gag (3, 6, 7, 11, 14, 15) is required for virus particles to be released from cell membranes of infected cells. Tsg101 is a member of the ESCRT-I complex of proteins involved in cell endosomal sorting. The ESCRT-I complex recruits proteins from the ESCRT-III complex with AIP1 (19), which provides the mechanical means for scission of virus particles from cell membranes. Thus, blocking the PT/SAP L-domain sequence from interacting with host ESCRT complex causes the virus budding defect and three lines of independent evidence support this idea. First, drugs targeted to this specific interaction in HIV-1 cause virus budding defects in infected cells without detectable off-target effects (5). Second, a research group identified noncoding SNPs in the 5' region of Tsg101 which correlate with viral load, implicating Tsg101-mediated viral particle release in disease progression (25). Third, viral infections activate a host innate immunity mechanism, through Interferon Stimulated Gene 15 (ISG15), that specifically disrupts virus budding complexes (1). In response to this immune system defense, many viruses encode enzymes that prevent or reverse ISG15 conjugation to cellular proteins to avoid the budding blockade (55-60). Taken together, this evidence indicates that targeting this interaction may lead to an effective antiviral strategy. Note that Pawliczek and Crump (31) have reported that HSV-1 production requires a functional ESCRT-III complex that could be independent of Tsg101 and Alix expression. However, there are multiple pathways to recruit ESCRT III proteins to functional virus budding complexes. For example, if we genetically replace the PT/SAP with the PPPPY L-domain in HIV-1 Gag, the virus still buds from cells independent of Tsg101 (10). Also, mutations of the HIV-1 L-domain in Gag causes a budding defect that can be rescued by overexpression of the specific ubiquitin ligase Nedd4L (12, 61). Nedd4L normally binds PPPPY motifs, which are absent from HIV-1 Gag. However, Nedd4 interacts with ESCRT-II proteins downstream from Tsg101, which in turn recruits the ESCRT-III proteins to the virus budding site (unpublished data). Thus, while Tsg101 is normally involved in recruiting the ESCRT-III complex, under stress its function can be replaced. This motivates our parallel investigation of small molecule inhibitors that target Nedd4's recruitment of the ESCRT-III complex. Independent of our work, Watanabe et al. (29) showed that release of a different herpes virus was susceptible to blockage by a prazole drug. They also used a HIV-1 Gag mutant bearing a disrupted PT/SAP motif (P7L-Gag) whose virus egress was independent of Tsg101 to demonstrate that release of this virus mutant was still blocked. This indicates that prazole drugs in particular are effective in blocking the budding process.

While the prazole analogs block the release of lenti and herpes viruses, the inhibition is manifested in different regions of the cell. The drugs block the release of HIV-1 at the outer cell membrane by preventing pinching of virus particles from the membrane (5). In contrast, herpesviruses, which assemble in the nucleus, appear to be first blocked at the passage of the virus through the nuclear membrane. Because the prazole drugs form a covalent bond to Tsg101, it strongly suggests that the ESCRT proteins are important for the herpesvirus particles to be released from the nucleus of the cell where they are formed. This is consistent with the recent report by Arii et al., (20) that the ESCRT-III protein complex mediates herpesvirus movement across the nuclear membrane and regulates its integrity. The finding that the prazole drugs cause a significant drop in total infectious herpesviruses reported here can be explained by the trapping of immature particles in the nucleus. This prevents them from migrating into the cytoplasm to exchange enveloped membranes, which makes them infectious. Also, the accumulation of the dense material in the nucleus observed in the electron micrographs suggests that prazole drugs may interfere with normal particle assembly in addition to blocking the passage of the particles through the nuclear membrane.

The use of prazoles represents an exciting potential case of repurposing existing drugs to act as antiviral therapeutic agents. Currently, omeprazole is marketed as a prodrug for treatment of acid reflux disease. Other prazole drugs are marketed for treatment of acid reflux disease in China, India, and South Korea (Yi Li An, Adiza, Noltec, respectively) indicating reasonable bioavailability and a known clinical safety profile. The prodrugs are acid-activated into derivatives that form disulfide linkages with proton pumps (26, 62, 63). The prodrug, but not the charged sulfonamide derivative, can cross the plasma membrane barrier. The antiviral activity of tenatoprazole has been suggested to be the result of forming a covalent disulfide bond with Tsg101 (5). While the binding site for tenatoprazole is near the ubiquitin (Ub) binding pocket and not the L-domain binding site, biochemical and confocal imaging data independently demonstrated that tenatoprazole disrupts the binding of Tsg101 to the PT/SAP sequence (5). While the precise biochemical mechanism remains to be clarified, our FTS results support that it may be related to allosteric changes in Tsg101 after the drug forms its covalent linkage with Cys73. Previous reports did not detect off-target effects of the prazole drugs affecting Tsg101 metabolism inside of cells (5). A possible exception is noted in an epidemiological study in a peer reviewed preprint in the American Journal of Gastroenterology by B. Spiegel and colleagues (64). In these studies, there was a small correlation between SARS-CoV-2 infections and patients taking commercially available prazole drugs, such as omeprazole, for acid reflux disease. However, this does not preclude the use of prazole compounds described in this paper. The drugs used by the patients, such as omeprazole, have weak antiviral activity (Table 2, shown in FIG. 6). In contrast, Ilaprazole have potent antiviral activity. At a dose of 10 mg of ilaprazole/day, plasma concentrations are around 2 µg h/ml, which is within the range needed for antiviral activity (65). The prazoles we tested here also appear to be nontoxic to Vero, HeLa, and 293T cells at the concentrations used to inhibit budding of herpesviruses and HIV-1. To improve potency of the prazole drugs, we have synthesized 53 analogs of ilaprazole. Several of these appear to have stronger binding to Tsg101 detected by the FTS assay. We are now testing these analogs to see if they have a more potent antiviral activity than ilaprazole.

A recent report highlighted the potential of prazole compounds to have a therapeutic effect on SARS-CoV-2 when combined with remdesivir (66). However, the authors did not definitively identify the mechanism of action of the prazoles and also concluded that the potency of the prazole compound used, omeprazole, is too low to reach therapeutic levels in vivo. A mechanism posed by the authors is that the prazoles lead to an increase in lysosomal pH, which is the potential mechanism for lysosomotropic drugs such as chloroquine (67). In contrast to omeprazole, we hypothesize that ilaprazole may allow for therapeutic levels to be reached in vivo. In the case of ilaprazole, which is marketed in several Asian countries as discussed above, our strong in vitro results lay the foundation for a potential fast-track to broad-spectrum antiviral clinical testing, alone or in combination with other drugs, in these countries. We are currently working to determine if ilaprazole or our novel compounds have activity against SARS-CoV-2 with or in combination with remdesivir. This would further the potential broad-spectrum antiviral capacity of the prazole compounds described in this report.

Materials and Methods

Viruses, plasmids, cell lines. Herpes simplex virus-1 (Kos strain), Herpes simplex virus-2(A/B-G), HIV plasmid PR9-HIV-1Ba-L (Center For AIDS Research [CFAR] Lab). pET-28b vector (Novagen-EMD Millipore), ROSETTA 2 (DE3) pLysS E. coli competent cells (EMD Millipore), Vero cells and 293T cell lines.

Chemicals. Prazole Compounds: Rabeprazole, Lansoprazole, Omeprazole, Ilaprazole, Dexlansoprazole, Tenatoprazole, and Pantoprazole were from SelleckChem. Omeprazole-N-Oxide and 4-Desmethoxy-omeprazole were from MolPort. Esomeprazole was from Toronto Research Chemicals.

Purification of Tsg101 (1-145). N-terminally His6-tagged Tsg101 UEV domain (amino acids 1-145), called Tsg101-UEV, was encoded in a pET-28b vector (Novagen—EMD Millipore), which also included a thrombin protease cleavage site (His6-Thrombin Site-Tsg101, 1-145). Tsg101-UEV was grown in LB broth with Kanamycin (30 µg/ml) in ROSETTA 2 (DE3) pLysS E. coli competent cells (EMD Millipore) and induced with 1 mM IPTG at room temperature for 3 h. Bacteria were collected by centrifugation at 4,000 rpm for 10 min at 40 C. Bacteria were suspended in 50 ml binding buffer (20 mM Tris-HCl, pH 7.9, 0.5 M NaCl, 5 mM Imidazole) with 1 mM PMSF, 0.1% NP40, and a Protease Inhibitor Cocktail Tablet (Roche) and sonicated for 3.5 min on ice. The sonicate was spun at 9,000 rpm for 1 h at 40 C in a Sorvall centrifuge. The supernatant was collected and passed through a 1.5 ml Ni-NTA Agarose column. The column was washed with 20 mM Tris-HCl, pH 7.9, 0.5 M NaCl, 30 mM Imidazole wash buffer. The column was then equilibrated with TEV cleavage buffer followed by 50 units of thrombin in the same buffer (Novagene). The column flow was stopped and incubated at room temperature overnight. The cleaved protein was eluted with wash buffer, and the protein dialyzed in D-tube Dialyzer Maxi, MWCO 12-14 kDa (Novagene) overnight against 0.15 M NaCl, 0.1 M HEPES, pH 7.5 buffer. The protein was concentrated in a MicroSep Advanced Centrifugal Device, 12-14 kDa exclusion (Pall) for 1 h at 1,300 rpm). Protein concentration was determined with a Nano Drop Spectrophotometer at 280 nM. When the His tag was not removed, the protein was eluted from the Ni-NTA column with 20 mM Tris-HCl, pH 7.9, 0.5 M NaCl, 1 M Imidazole. The protein was evaluated by SDS-PAGE gel for purity.

Fluorescence thermal shift (FTS) screening to identify small molecule binding to Tsg101-UEV. FTS monitors protein thermal denaturation using environment-sensitive dye Sypro-Orange which fluoresces when bound to hydrophobic surfaces, taking advantage of the changes in hydrophobic surface exposure in protein denaturation. Discovery of small molecule binding to target protein utilizes the observation that ligand binding affects protein thermal stability, and therefore can be detected through a shift in the protein's thermal denaturation (melting) temperature (Tm). We have employed FTS to reveal changes in thermodynamic properties of Tsg101 elicited by its interaction with a small molecule. The recombinant Tsg101 fragment (amino acids 1-145), prepared as described above in Materials and Methods (but without label) has a thermal unfolding profile suitable for using FTS as a primary screen assay in HTS. A fluorescence dye Sypro-Orange (Invitrogen) was used for assay detection. The dye is excited at 473 nm and has a fluorescence emission at 610 nm. The dye binds to hydrophobic regions of a protein that are normally buried in a native protein structure. When a protein is unfolded, the dye interacts with exposed hydrophobic surfaces and the fluorescence intensity increases significantly over that observed in aqueous solution. The Tsg101 fragment was premixed at a concentration of 2 µM with a 5× concentration of Sypro-Orange in HEPES buffer (100 mM HEPES, 150 mM NaCl, pH 7.5). Then 10 µl of the protein-dye mix was added to an assay plate and 10 to 50 nanoliters of compound, equal to 10 to 50 µM, were added with an acoustic transfer robot Echo550 (Labcyte, CA). The plate was shaken to ensure proper mixing, then sealed with an optical seal and centrifuged. The thermal scan was performed from 20 to 90° C. with a temperature ramp rate of 0.5° C./min. Fluorescence was detected on a real-time PCR machine CFX384 (Bio-Rad Laboratories). Comparison of the thermal denaturation profile for Tsg101-UEV in the presence and absence of tenatoprazole and other prazoles revealed destabilization of the native protein structure, indicating that the compound interacted with Tsg101-UEV.

Herpesvirus infection of Vero cells. Vero cells (0.8×106 cells/well of a 6-well plate) were infected with HSV-1 or HSV-2 at a MOI of 0.1 pfu/cell in DMEM with 1% serum for two hours in the C02 incubator at 37° C. In one experiment looking at the effect of tenatoprazole on HSV-2 release from cells 24 and 48 h a MOI of 3 pfu/cell was used. The cell supernatants were aspirated and replaced with 1 ml (24 h) or 2 ml (48 h and 72 h) of DMEM with 1% serum with DMSO or different concentrations of drug (tenatoprazole, ilaprazole, or analogs) dissolved in DMSO. After 24 or 48 h incubation, the cell supernatant was collected and frozen at −80° C. Virus titer in the cell media fraction was determined by standard plaque assays using 10-fold serial dilutions of cell supernatants of Vero cells and incubated for 48 h after which cells were fixed and stained to count the plaques (22). For determination of total virus (extracellular+cytoplasmic), virus infected cells were incubated for 24 h with and without drug presence, then the plate of cells were subjected to 3 cycles of freeze/thawing (−80° C./37° C.) 30 min each prior to collecting the supernatant after centrifugation for measurement of total virus titer. Virus titer was measured by standard plaque assay as above. For analyzing the effect of benserazide (K21) at different concentrations on release of HSV-1 from VERO cells, experiments were repeated 4 times each and did not appear to affect release of virus from cells. In separate experiments, uninfected Vero cells were carried for 3 weeks in culture in the presence or absence of drugs (replaced every third day) and found to exhibit the same growth rate detected with a light microscope.

HIV-1 transfection of 293T cells. 293T cells (American Type Culture Collection) were grown in a 24-well Clear Flat Bottom TC-treated Multiwell Cell Culture Plate using Dulbecco's modified Eagle's medium (Cellgro) containing fetal bovine serum (10%), 100 U/ml penicillin, 100 µg/ml streptomycin, and 292 µg/ml 1-glutamine (Cellgro). Cells were grown to 60-70% confluency at 37° C. and 5% CO2 prior to addition of drug treatment. Culture media was aspirated and replaced with media containing drug compound 7 hours prior to transfection of the plasmid encoding the HIV-1 genome. Transfection was done using reagent Polyethyleneimine (PEI, Polysciences). For production of virus particles, cells were transfected with pR9-HIV-1Ba-L plasmid. After 24 h and 48 h, tissue culture media was collected and passed through a 0.45-micron filter. Virus released from cells was quantified by media-associated p24 determined using fluorescently tagged CA targeting antibody (PerkinElmer) and equivalent amounts of p24 as standards.

Drug potency and cell toxicity. EC50 calculations were determined by using AAT Bioquest's EC50 calculator. Cell toxicity at different concentrations of drugs as indicated was determine using the Cell Proliferation Reagent WST-1 (Roche Diagnostics) or cellular 96® Aqueous One Reagent viability reagent according to manufacturer's instructions. For 293T cells, the concentration of DMSO was 0.2% or less and assays were carried out with DMEM with 10% serum. Cell toxicity experiments were repeated twice.

Transmission electron Microscopy. Vero cells on glass cover slips were infected with HSV-2 at a MOI of 0.1 for two hours. Then 105 µM of tenatoprazole or 18 µM Ilaprazole was added and cells incubated for 24 hours. Tissue samples were fixed in 0.1 M sodium cacodylate buffer pH 7.3 containing 2% paraformaldehyde and 2.5% glutaraldehyde and post-fixed with 2% osmium tetroxide in unbuffered aqueous solution. The samples were rinsed with distilled water, en bloc stained with 3% uranyl acetate, rinsed with distilled water, dehydrated in ascending grades of ethanol, transitioned with propylene oxide, embedded in the resin mixture of Embed 812 kit and cured in a 60° C. oven. Samples were sectioned on a Leica Ultracut UC6 ultramicrotome. 1 µm thick sections were collected and stained with Toluidine Blue O and 70 nm sections were collected on 200 mesh copper grids; thin sections were stained with uranyl acetate and Reynolds lead citrate. Transmission electron microscopy (TEM) was performed on a FEI Tecnai Spirit G2.

REFERENCES

1. Seo E J, Leis J. 2012. Budding of Enveloped Viruses: Interferon-Induced ISG15—Antivirus Mechanisms Targeting the Release Process. Advances in virology 2012.
2. Carlton J G, Martin-Serrano J. 2007. Parallels between cytokinesis and retroviral budding: a role for the ESCRT machinery. Science 316:1908-1912.
3. Gottlinger H G, Dorfman T, Sodroski J G, Haseltine W A. 1991. Effect of mutations affecting the p6 gag protein on human immunodeficiency virus particle release. Proc Natl Acad Sci USA 88:3195-9.
4. Pincetic A, Medina G, Carter C, Leis J. 2008. Avian sarcoma virus and human immunodeficiency virus, type 1 use different subsets of ESCRT proteins to facilitate the budding process. Journal of Biological Chemistry 283: 29822-29830.
5. Strickland M, Ehrlich L S, Watanabe S, Khan M, Strub M P, Luan C H, Powell M D, Leis J, Tjandra N, Carter C A. 2017. Tsg101 chaperone function revealed by HIV-1 assembly inhibitors. Nat Commun 8:1391.
6. Wills J W, Cameron C E, Wilson C B, Xiang Y, Bennett R P, Leis J. 1994. An assembly domain of the Rous sarcoma virus Gag protein required late in budding. J Virol 68:6605-18.
7. Xiang Y, Cameron C E, Wills J W, Leis J. 1996. Fine mapping and characterization of the Rous sarcoma virus Pr76gag late assembly domain. J Virol 70:5695-700.
8. Medina G, Pincetic A, Ehrlich L S, Zhang Y, Tang Y, Leis J, Carter C A. 2008. Tsg101 can replace Nedd4 function in ASV Gag release but not membrane targeting. Virology 377:30-38.
9. Taylor G M, Hanson P I, Kielian M. 2007. Ubiquitin depletion and dominant-negative VPS4 inhibit rhabdovirus budding without affecting alphavirus budding. Journal of virology 81:13631-13639.
10. Medina G, Zhang Y, Tang Y, Gottwein E, Vana M L, Bouamr F, Leis J, Carter C A. 2005. The functionally exchangeable L domains in RSV and HIV-1 Gag direct particle release through pathways linked by Tsg101. Traffic 6:880-894.
11. VerPlank L, Agresta B, Grassa T, Kikonyogo A, Leis J, Carter C. 2001. Tsg101, the prototype of a class of dominant-negative ubiquitin regulators, binds human immunodeficiency virus type 1 Pr55Gag: the L domain is a determining of binding. Proc Natl Acad Sci USA 98:7724-7729.
12. Chung H Y, Morita E, von Schwedler U, Muller B, Krausslich H G, Sundquist W I. 2008. NEDD4L overexpression rescues the release and infectivity of human immunodeficiency virus type 1 constructs lacking PTAP and YPXL late domains. J Virol 82:4884-97.
13. Fujii K, Munshi U M, Ablan S D, Demirov D G, Soheilian F, Nagashima K, Stephen A G, Fisher R J, Freed E O. 2009. Functional role of Alix in HIV-1 replication. Virology 391:284-292.
14. Garrus J E, von Schwedler U K, Pornillos O W, Morham S G, Zavitz K H, Wang H E, Wettstein D A, Stray K M, Cote M, Rich R L, Myszka D G, Sundquist W I. 2001. Tsg101 and the vacuolar protein sorting pathway are essential for HIV-1 budding. Cell 107:55-65.
15. Goff A, Ehrlich L S, Cohen S N, Carter C A. 2003. Tsg101 control of human immunodeficiency virus type 1 Gag trafficking and release. J Virol 77:9173-82.
16. Martin-Serrano J, Yaravoy A, Perez-Caballero D, Bieniasz P D. 2003. Divergent retroviral late-budding domains recruit vacular protein sorting factors by using alternative adaptor proteins. Proceedings of the National Academy of Sciences 100:12414-12419.

17. Pornillos O, Alam S L, Rich R L, Myszka D G, Davis D R, Sundquist W I. 2002. Structure and functional interactions of the Tsg101 UEV domain. The EMBO journal 21:2397-2406.
18. von Schwedler U K, Stuchell M, Muller B, Ward D M, Chung H Y, Morita E, Wang H E, Davis T, He G P, Cimbora D M, Scott A, Krausslich H G, Kaplan J, Morham S G, Sundquist W I. 2003. The protein network of HIV budding. Cell 114:701-13.
19. Strack B, Calistri A, Craig S, Popova E, Gottlinger H G. 2003. AIP1/ALIX is a binding partner for HIV-1 p6 and EIAV p9 functioning in virus budding. Cell 114:689-699.
20. Arii J, Watanabe M, Maeda F, Tokai-Nishizumi N, Chihara T, Miura M, Maruzuru Y, Koyanagi N, Kato A, Kawaguchi Y. 2018. ESCRT-III mediates budding across the inner nuclear membrane and regulates its integrity. Nat Commun 9:3379.
21. Lee C P, Liu P T, Kung F I N, Su M T, Chua H H, Chang Y H, Chang C W, Tsai C H, Liu F T, Chen M R. 2012. The ESCRT machinery is recruited by the viral BFRF1 protein to the nucleus-associated membrane for the maturation of Epstein-Barr Virus. PLoS Pathog 8:e1002904.
22. Kuang Z, Seo E J, Leis J. 2011. Mechanism of inhibition of retrovirus release from cells by interferon-induced gene ISG15. Journal of virology 85:7153-7161.
23. Pincetic A, Leis J. 2009. The Mechanism of Budding of Retroviruses From Cell Membranes. Adv Virol 2009:6239691-6239699.
24. Pincetic A, Kuang Z, Seo E J, Leis J. 2010. The interferon-induced gene ISG15 blocks retrovirus release from cells late in the budding process. J Virol 84:4725-36.
25. Bashirova A A, Bleiber G, Qi Y, Hutcheson H, Yamashita T, Johnson R C, Cheng J, Alter G, Goedert J J, Buchbinder S, Hoots K, Vlahov D, May M, Maldarelli F, Jacobson L, O'Brien S J, Telenti A, Carrington M. 2006. Consistent effects of TSG101 genetic variability on multiple outcomes of exposure to human immunodeficiency virus type 1. J Virol 80:6757-63.
26. Shin J M, Kim N. 2013. Pharmacokinetics and pharmacodynamics of the proton pump inhibitors. J Neurogastroenterol Motil 19:25-35.
27. Luan C-H, Light S H, Dunne S F, Anderson W F. 2014. Ligand screening using fluorescence thermal shift analysis (FTS), p 263-289, Structural Genomics and Drug Discovery. Springer.
28. Pantoliano M W, Petrella E C, Kwasnoski J D, Lobanov V S, Myslik J, Graf E, Carver T, Asel E, Springer B A, Lane P, Salemme F R. 2001. High-density miniaturized thermal shift assays as a general strategy for drug discovery. J Biomol Screen 6:429-40.
29. Watanabe S M, Ehrlich L S, Strickland M, Li X, Soloveva V, Goff A J, Stauft C B, Bhaduri-McIntosh S, Tjandra N, Carter C. 2020. Selective Targeting of Virus Replication by Proton Pump Inhibitors. Sci Rep 10:4003.
30. Lee S K, Longnecker R. 1997. The Epstein-Barr virus glycoprotein 110 carboxy-terminal tail domain is essential for lytic virus replication. Journal of virology 71:4092-4097.
31. Pawliczek T, Crump C M. 2009. Herpes simplex virus type 1 production requires a functional ESCRT-III complex but is independent of TSG101 and ALIX expression. Journal of virology 83:11254-11264.
32. Calistri A, Sette P, Salata C, Cancellotti E, Forghieri C, Comin A, Gottlinger H, Campadelli-Fiume G, Palú G, Parolin C. 2007. Intracellular trafficking and maturation of herpes simplex virus type 1 gB and virus egress require functional biogenesis of multivesicular bodies. Journal of virology 81:11468-11478.
33. Calistri A, Munegato D, Toffoletto M, Celestino M, Franchin E, Comin A, Sartori E, Salata C, Parolin C, Palu G. 2015. Functional Interaction Between the ESCRT-I Component TSG101 and the HSV-1 Tegument Ubiquitin Specific Protease. Journal of cellular physiology 230:1794-1806.
34. Crump C M, Yates C, Minson T. 2007. Herpes simplex virus type 1 cytoplasmic envelopment requires functional Vps4. Journal of virology 81:7380-7387.
35. Tandon R, AuCoin D P, Mocarski E S. 2009. Human cytomegalovirus exploits ESCRT machinery in the process of virion maturation. J Virol 83:10797-807.
36. Perez M, Craven R C, de la Torre J C. 2003. The small RING finger protein Z drives arenavirus budding: implications for antiviral strategies. Proc Natl Acad Sci USA 100:12978-83.
37. Urata S, Noda T, Kawaoka Y, Yokosawa H, Yasuda J. 2006. Cellular factors required for Lassa virus budding. Journal of virology 80:4191-4195.
38. Ariumi Y, Kuroki M, Maki M, Ikeda M, Dansako H, Wakita T, Kato N. 2011. The ESCRT system is required for hepatitis C virus production. PloS one 6.
39. Corless L, Crump C M, Griffin S D, Harris M. 2010. Vps4 and the ESCRT-III complex are required for the release of infectious hepatitis C virus particles. Journal of General Virology 91:362-372.
40. Han Z, Lu J, Liu Y, Davis B, Lee M S, Olson M A, Ruthel G, Freedman B D, Schnell M J, Wrobel J E. 2014. Small-molecule probes targeting the viral PPxY-host Nedd4 interface block egress of a broad range of RNA viruses. Journal of virology 88:7294-7306.
41. Harty R N, Brown M E, Wang G, Huibregtse J, Hayes F P. 2000. A PPxY motif within the VP40 protein of Ebola virus interacts physically and functionally with a ubiquitin ligase: implications for Filovirus budding. Proceedings of the National Academy of Sciences 97:13871-13876.
42. Lu J, Han Z, Liu Y, Liu W, Lee M S, Olson M A, Ruthel G, Freedman B D, Harty R N. 2014. A host-oriented inhibitor of Junin Argentine hemorrhagic fever virus egress. Journal of virology 88:4736-4743.
43. Madara J J, Han Z, Ruthel G, Freedman B D, Harty R N. 2015. The multifunctional Ebola virus VP40 matrix protein is a promising therapeutic target. Future virology 10:537-546.
44. Martin-Serrano J, Zang T, Bieniasz P D. 2001. HIV-1 and Ebola virus encode small peptide motifs that recruit Tsg101 to sites of particle assembly to facilitate egress. Nature medicine 7:1313-1319.
45. Silvestri L S, Ruthel G, Kallstrom G, Warfield K L, Swenson D L, Nelle T, Iversen P L, Bavari S, Aman M J. 2007. Involvement of vacuolar protein sorting pathway in Ebola virus release independent of TSG101 interaction. J Infect Dis 196 Suppl 2:S264-70.
46. Timmins J, Schoehn G, Ricard-Blum S, Scianimanico S, Vernet T, Ruigrok R W, Weissenhorn W. 2003. Ebola virus matrix protein VP40 interaction with human cellular factors Tsg101 and Nedd4. J Mol Biol 326:493-502.
47. Urata S, Noda T, Kawaoka Y, Morikawa S, Yokosawa H, Yasuda J. 2007. Interaction of Tsg101 with Marburg virus VP40 depends on the PPPY motif, but not the PT/SAP motif as in the case of Ebola virus, and Tsg101 plays a critical role in the budding of Marburg virus-like particles induced by VP40, NP, and GP. J Virol 81:4895-9.

48. Lambert C, Döring T, Prange R. 2007. Hepatitis B virus maturation is sensitive to functional inhibition of ESCRT-III, Vps4, and γ2-adaptin. Journal of virology 81:9050-9060.
49. Li M, Schmitt P T, Li Z, McCrory T S, He B, Schmitt A P. 2009. Mumps virus matrix, fusion, and nucleocapsid proteins cooperate for efficient production of virus-like particles. Journal of virology 83:7261-7272.
50. Schmitt A P, Leser G P, Morita E, Sundquist W I, Lamb R A. 2005. Evidence for a new viral late-domain core sequence, FPIV, necessary for budding of a paramyxovirus. J Virol 79:2988-97.
51. Schmitt A P, Leser G P, Waning D L, Lamb R A. 2002. Requirements for budding of paramyxovirus simian virus 5 virus-like particles. J Virol 76:3952-64.
52. Irie T, Harty R N. 2005. L-domain flanking sequences are important for host interactions and efficient budding of vesicular stomatitis virus recombinants. Journal of virology 79:12617-12622.
53. Wirblich C, Tan G S, Papaneri A, Godlewski P J, Orenstein J M, Harty R N, Schnell M J. 2008. PPEY motif within the rabies virus (RV) matrix protein is essential for efficient virion release and RV pathogenicity. Journal of virology 82:9730-9738.
54. Gordon C J, Tchesnokov E P, Feng J Y, Porter D P, Gotte M. 2020. The antiviral compound remdesivir potently inhibits RNA-dependent RNA polymerase from Middle East respiratory syndrome coronavirus. J Biol Chem 295:4773-4779.
55. Arguello M D, Hiscott J. 2007. Ub surprised: viral ovarian tumor domain proteases remove ubiquitin and ISG15 conjugates. Cell Host Microbe 2:367-9.
56. Frias-Staheli N, Giannakopoulos N V, Kikkert M, Taylor S L, Bridgen A, Paragas J, Richt J A, Rowland R R, Schmaljohn C S, Lenschow D J. 2007. Ovarian tumor domain-containing viral proteases evade ubiquitin- and ISG15-dependent innate immune responses. Cell host & microbe 2:404-416.
57. Harty R N, Pitha P M, Okumura A. 2009. Antiviral activity of innate immune protein ISG15. Journal of innate immunity 1:397-404.
58. Vana M L, Tang Y, Chen A, Medina G, Carter C, Leis J. 2004. Role of Nedd4 and ubiquitination of Rous sarcoma virus Gag in budding of virus-like particles from cells. Journal of virology 78:13943-13953.
59. Yuan W, Aramini J M, Montelione G T, Krug R M. 2002. Structural basis for ubiquitin-like ISG 15 protein binding to the NS1 protein of influenza B virus: a protein—protein interaction function that is not shared by the corresponding N-terminal domain of the NS1 protein of influenza A virus. Virology 304:291-301.
60. Yuan W, Krug R M. 2001. Influenza B virus NS1 protein inhibits conjugation of the interferon (IFN)-induced ubiquitin-like ISG15 protein. EMBO J 20:362-71.
61. Usami Y, Popov S, Popova E, Gottlinger H G. 2008. Efficient and specific rescue of human immunodeficiency virus type 1 budding defects by a Nedd4-like ubiquitin ligase. J Virol 82:4898-907.
62. Kakinoki B, Ono C, Yamazaki N, Chikamatsu N, Wakatsuki D, Uchiyama K, Morinaka Y. 1999. General pharmacological properties of the new proton pump inhibitor (+/−)-5-methoxy-2-[[(4-methoxy-3, 5-dimethylpyrid-2-yl) methyl] sulfi-nyl]-1H-imidazo [4, 5-b] pyridine. Methods Find Exp Clin Pharmacol 21:179-187.
63. Shin J M, Sachs G. 2002. Restoration of acid secretion following treatment with proton pump inhibitors. Gastroenterology 123:1588-97.
64. Chistopher V. Almario W D C, Brennan M. R. Spiegel. 2020. Increased Risk of COVID-19 Among Users of Proton Pump Inhibitors. American Journal of Gastroenterology Preprint.
65. de Bortoli N, Martinucci I, Giacchino M, Blandizzi C, Marchi S, Savarino V, Savarino E. 2013. The pharmacokinetics of ilaprazole for gastro-esophageal reflux treatment. Expert Opin Drug Metab Toxicol 9:1361-9.
66. Bojkova D, McGreig J E, McLaughlin K-M, Masterson S G, Widera M, Kraehling V, Ciesek S, Wass M N, Michaelis M, Cinatl J N. 2020. SARS-CoV-2 and SARS-CoV differ in their cell tropism and drug sensitivity profiles. bioRxiv.
67. Al-Bari M A A. 2017. Targeting endosomal acidification by chloroquine analogs as a promising strategy for the treatment of emerging viral diseases. Pharmacol Res Perspect 5:e00293.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method of treating an infection by an enveloped virus in a patient, the method comprising administering to the patient a pharmaceutical composition comprising a compound of a formula:

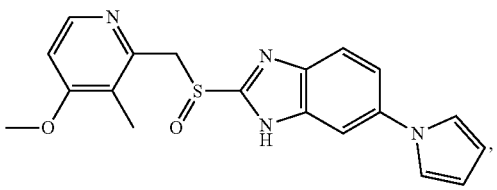 [SMILES: COc1ccnc(CS(=O)c2nc3ccc(-n4cccc4)cc3[nH]2)c1C]

wherein the enveloped virus is selected from herpes simplex virus type 1, herpes simplex virus type 2, and human immunodeficiency virus (HIV).

2. The method of claim 1, wherein the enveloped virus is herpes simplex virus type 1.

3. The method of claim 1, wherein the enveloped virus is herpes simplex virus type 2.

4. The method of claim 1, wherein the enveloped virus is human immunodeficiency virus (HIV).

5. The method of claim 1, wherein the compound has antiviral activity against the enveloped virus selected from (i) inhibiting formation of an associative complex, (ii) disrupting formation of an associative complex, and (iii) both of (i) and (ii), wherein the associative complex comprises an L-domain motif of the enveloped virus and at least one cellular polypeptide, or fragment thereof, capable of binding the L-domain motif of the enveloped virus.

6. The method of claim 5, wherein the L-domain motif comprises at least one of a PY-motif or a PTAP-motif.

7. The method of claim 5, wherein the L-domain motif comprises at least one amino acid sequence selected from the group consisting of SEQ ID NOS: 6, 7, and 12.

8. The method of claim 5, wherein the at least one cellular polypeptide comprises an ESCRT complex protein.

9. The method of claim 8, wherein the ESCRT component protein comprises at least one member selected from a Nedd 4-related family peptide or a fragment thereof, TSG101 or a fragment thereof, and combinations thereof.

10. The method of claim 8, wherein the ESCRT component protein comprises at least one amino acid sequence selected from the group consisting of SEQ ID NOS: 23, 24, 25 and 26.

11. A method of inhibiting release of an enveloped virus from a cell, the method comprising contacting the cell with a compound of a formula:

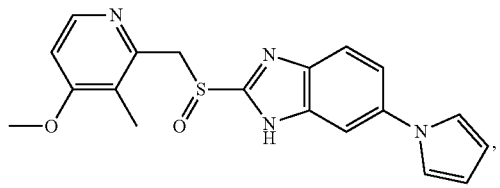

wherein the enveloped virus is selected from herpes simplex virus type 1, herpes simplex virus type 2, and human immunodeficiency virus (HIV).

12. The method of claim 11, wherein the enveloped virus is herpes simplex virus type 1.

13. The method of claim 11, wherein the enveloped virus is herpes simplex virus type 2.

14. The method of claim 11, wherein the enveloped virus is human immunodeficiency virus (HIV).

15. The method of claim 11, wherein the compound has antiviral activity against the enveloped virus selected from (i) inhibiting formation of an associative complex, (ii) disrupting formation of an associative complex, and (iii) both of (i) and (ii), wherein the associative complex comprises an L-domain motif of the enveloped virus and at least one cellular polypeptide, or fragment thereof, capable of binding the L-domain motif of the enveloped virus.

16. The method of claim 15, wherein the L-domain motif comprises at least one of a PY-motif or a PTAP-motif.

17. The method of claim 15, wherein the L-domain motif comprises at least one amino acid sequence selected from the group consisting of SEQ ID NOS: 6, 7, and 12.

18. The method of claim 15, wherein the at least one cellular polypeptide comprises an ESCRT complex protein.

19. The method of claim 18, wherein the ESCRT component protein comprises at least one member selected from a Nedd 4-related family peptide or a fragment thereof, TSG101 or a fragment thereof, and combinations thereof.

20. The method of claim 18, wherein the ESCRT component protein comprises at least one amino acid sequence selected from the group consisting of SEQ ID NOS: 23, 24, 25 and 26.

* * * * *

SEQUENCE LISTING

```
<160> NUMBER OF SEQ ID NOS: 26

<210> SEQ ID NO 1
<211> LENGTH: 20
<212> TYPE: PRT
<213> ORGANISM: Artificial Sequence
<220> FEATURE:
<223> OTHER INFORMATION: Synthetic- Viral L-domain motif
```

```
<400> SEQUENCE: 1

Ala Ala Pro Thr Ala Pro Pro Thr Gly Ala Ala Asp Ser Ile Pro Pro
1               5                   10                  15

Pro Tyr Ser Pro
            20

<210> SEQ ID NO 2
<211> LENGTH: 11
<212> TYPE: PRT
<213> ORGANISM: Artificial Sequence
<220> FEATURE:
<223> OTHER INFORMATION: Synthetic- Viral L-domain motif

<400> SEQUENCE: 2

Thr Ala Pro Ser Ser Pro Pro Tyr Glu Glu
1               5                   10

<210> SEQ ID NO 3
<211> LENGTH: 17
<212> TYPE: PRT
<213> ORGANISM: Artificial Sequence
<220> FEATURE:
<223> OTHER INFORMATION: Synthetic- Viral L-domain motif

<400> SEQUENCE: 3

Met Arg Arg Val Ile Leu Pro Thr Ala Pro Pro Glu Tyr Met Glu Ala
1               5                   10                  15

Ile

<210> SEQ ID NO 4
<211> LENGTH: 16
<212> TYPE: PRT
<213> ORGANISM: Artificial Sequence
<220> FEATURE:
<223> OTHER INFORMATION: Synthetic- Viral L-domain motif

<400> SEQUENCE: 4

Asn Thr Tyr Met Gln Tyr Leu Asn Pro Pro Pro Tyr Ala Asp His Ser
1               5                   10                  15

<210> SEQ ID NO 5
<211> LENGTH: 4
<212> TYPE: PRT
<213> ORGANISM: Artificial Sequence
<220> FEATURE:
<223> OTHER INFORMATION: Synthetic- Viral L-domain motif

<400> SEQUENCE: 5

Pro Pro Ala Tyr
1

<210> SEQ ID NO 6
<211> LENGTH: 4
<212> TYPE: PRT
<213> ORGANISM: Artificial Sequence
<220> FEATURE:
<223> OTHER INFORMATION: Synthetic- Viral L-domain motif

<400> SEQUENCE: 6

Pro Pro Thr Tyr
1

<210> SEQ ID NO 7
<211> LENGTH: 4
```

```
<212> TYPE: PRT
<213> ORGANISM: Artificial Sequence
<220> FEATURE:
<223> OTHER INFORMATION: Synthetic- Viral L-domain motif

<400> SEQUENCE: 7

Pro Pro Pro Tyr
1

<210> SEQ ID NO 8
<211> LENGTH: 4
<212> TYPE: PRT
<213> ORGANISM: Artificial Sequence
<220> FEATURE:
<223> OTHER INFORMATION: Synthetic- Viral L-domain motif

<400> SEQUENCE: 8

Pro Thr Ala Pro
1

<210> SEQ ID NO 9
<211> LENGTH: 14
<212> TYPE: PRT
<213> ORGANISM: Artificial Sequence
<220> FEATURE:
<223> OTHER INFORMATION: Synthetic- Viral L-domain motif

<400> SEQUENCE: 9

Gln Ser Ile Lys Ala Phe Pro Ile Val Ile Asn Ser Asp Gly
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic- Viral L-domain motif

<400> SEQUENCE: 10

Arg Leu Asn Ala Phe Pro Ile Val Met Gly Gln
1               5                   10

<210> SEQ ID NO 11
<211> LENGTH: 19
<212> TYPE: PRT
<213> ORGANISM: Artificial Sequence
<220> FEATURE:
<223> OTHER INFORMATION: Synthetic- Viral L-domain motif

<400> SEQUENCE: 11

Ala Thr Ala Ser Ala Pro Pro Pro Tyr Val Gly Ser Gly Leu Tyr
1               5                   10                  15

Pro Ser Leu

<210> SEQ ID NO 12
<211> LENGTH: 22
<212> TYPE: PRT
<213> ORGANISM: Artificial Sequence
<220> FEATURE:
<223> OTHER INFORMATION: Synthetic- Viral L-domain motif

<400> SEQUENCE: 12

Pro Glu Pro Thr Ala Pro Pro Phe Leu Gln Ser Arg Pro Glu Pro Thr
1               5                   10                  15

Ala Pro Pro Glu Glu Ser
            20
```

<210> SEQ ID NO 13
<211> LENGTH: 14
<212> TYPE: PRT
<213> ORGANISM: Artificial Sequence
<220> FEATURE:
<223> OTHER INFORMATION: Synthetic- Viral L-domain motif

<400> SEQUENCE: 13

Asp Pro Gln Ile Pro Pro Pro Tyr Val Glu Pro Thr Ala Pro
1               5                   10

<210> SEQ ID NO 14
<211> LENGTH: 11
<212> TYPE: PRT
<213> ORGANISM: Artificial Sequence
<220> FEATURE:
<223> OTHER INFORMATION: Synthetic- Viral L-domain motif

<400> SEQUENCE: 14

Gln Asn Leu Tyr Pro Asp Leu Ser Glu Ile Lys
1               5                   10

<210> SEQ ID NO 15
<211> LENGTH: 21
<212> TYPE: PRT
<213> ORGANISM: Artificial Sequence
<220> FEATURE:
<223> OTHER INFORMATION: Synthetic- Viral L-domain motif

<400> SEQUENCE: 15

Leu Gly Ile Ala Pro Pro Pro Tyr Glu Glu Asp Thr Ser Met Glu Tyr
1               5                   10                  15

Ala Pro Ser Ala Pro
            20

<210> SEQ ID NO 16
<211> LENGTH: 16
<212> TYPE: PRT
<213> ORGANISM: Artificial Sequence
<220> FEATURE:
<223> OTHER INFORMATION: Synthetic- Viral L-domain motif

<400> SEQUENCE: 16

Asp Asp Leu Trp Leu Pro Pro Pro Glu Tyr Val Pro Leu Lys Glu Leu
1               5                   10                  15

<210> SEQ ID NO 17
<211> LENGTH: 48
<212> TYPE: PRT
<213> ORGANISM: Artificial Sequence
<220> FEATURE:
<223> OTHER INFORMATION: Synthetic- Viral L-domain motif

<400> SEQUENCE: 17

Ala Thr Ala Ser Ala Pro Pro Tyr Val Gly Ser Gly Gly Gly Ala
1               5                   10                  15

Thr Ala Ser Ala Pro Pro Pro Tyr Val Gly Ser Gly Gly Gly Ala Thr
            20                  25                  30

Ala Ser Ala Pro Pro Pro Tyr Val Gly Ser Gly Gly Gly Arg Arg Arg
            35                  40                  45

<210> SEQ ID NO 18
<211> LENGTH: 48
<212> TYPE: PRT

```
<213> ORGANISM: Artificial Sequence
<220> FEATURE:
<223> OTHER INFORMATION: Synthetic- Viral L-domain motif
<220> FEATURE:
<221> NAME/KEY: MISC_FEATURE
<222> LOCATION: (1)..(1)
<223> OTHER INFORMATION: FITC-MODIFIED N-TERMINUS

<400> SEQUENCE: 18

Ala Thr Ala Ser Ala Pro Pro Tyr Val Gly Ser Gly Gly Gly Ala
1               5                   10                  15

Thr Ala Ser Ala Pro Pro Pro Tyr Val Gly Ser Gly Gly Gly Ala Thr
            20                  25                  30

Ala Ser Ala Pro Pro Pro Tyr Val Gly Ser Gly Gly Gly Arg Arg Arg
        35                  40                  45

<210> SEQ ID NO 19
<211> LENGTH: 48
<212> TYPE: PRT
<213> ORGANISM: Artificial Sequence
<220> FEATURE:
<223> OTHER INFORMATION: Synthetic- Viral L-domain motif
<220> FEATURE:
<221> NAME/KEY: MISC_FEATURE
<222> LOCATION: (1)..(1)
<223> OTHER INFORMATION: TAMRA-MODIFIED N-TERMINUS

<400> SEQUENCE: 19

Ala Thr Ala Ser Ala Pro Pro Tyr Val Gly Ser Gly Gly Gly Ala
1               5                   10                  15

Thr Ala Ser Ala Pro Pro Pro Tyr Val Gly Ser Gly Gly Gly Ala Thr
            20                  25                  30

Ala Ser Ala Pro Pro Pro Tyr Val Gly Ser Gly Gly Gly Arg Arg Arg
        35                  40                  45

<210> SEQ ID NO 20
<211> LENGTH: 36
<212> TYPE: PRT
<213> ORGANISM: Artificial Sequence
<220> FEATURE:
<223> OTHER INFORMATION: Synthetic- Viral L-domain motif

<400> SEQUENCE: 20

Arg Pro Gly Asn Phe Leu Gln Ser Arg Pro Glu Pro Thr Ala Pro Pro
1               5                   10                  15

Phe Leu Gln Ser Arg Pro Glu Pro Thr Ala Pro Pro Glu Glu Ser Phe
            20                  25                  30

Arg Arg Arg Arg
        35

<210> SEQ ID NO 21
<211> LENGTH: 36
<212> TYPE: PRT
<213> ORGANISM: Artificial Sequence
<220> FEATURE:
<223> OTHER INFORMATION: Synthetic- Viral L-domain motif
<220> FEATURE:
<221> NAME/KEY: MISC_FEATURE
<222> LOCATION: (1)..(1)
<223> OTHER INFORMATION: FITC-MODIFIED N-TERMINUS

<400> SEQUENCE: 21

Arg Pro Gly Asn Phe Leu Gln Ser Arg Pro Glu Pro Thr Ala Pro Pro
1               5                   10                  15

Phe Leu Gln Ser Arg Pro Glu Pro Thr Ala Pro Pro Glu Glu Ser Phe
```

-continued

```
                20                  25                  30

Arg Arg Arg Arg
         35

<210> SEQ ID NO 22
<211> LENGTH: 36
<212> TYPE: PRT
<213> ORGANISM: Artificial Sequence
<220> FEATURE:
<223> OTHER INFORMATION: Synthetic- Viral L-domain motif
<220> FEATURE:
<221> NAME/KEY: MISC_FEATURE
<222> LOCATION: (1)..(1)
<223> OTHER INFORMATION: TAMRA-MODIFIED N-TERMINUS

<400> SEQUENCE: 22

Arg Pro Gly Asn Phe Leu Gln Ser Arg Pro Glu Pro Thr Ala Pro Pro
1               5                  10                  15

Phe Leu Gln Ser Arg Pro Glu Pro Thr Ala Pro Pro Glu Glu Ser Phe
                20                  25                  30

Arg Arg Arg Arg
         35

<210> SEQ ID NO 23
<211> LENGTH: 879
<212> TYPE: PRT
<213> ORGANISM: Artificial Sequence
<220> FEATURE:
<223> OTHER INFORMATION: WWP2 RECOMBINANT PROTEIN

<400> SEQUENCE: 23

Met Asp Tyr Lys Asp Asp Asp Lys Met Ala Ser Ala Ser Ser Ser
1               5                  10                  15

Arg Ala Gly Val Ala Leu Pro Phe Glu Lys Ser Gln Leu Thr Leu Lys
                20                  25                  30

Val Val Ser Ala Lys Pro Lys Val His Asn Arg Gln Pro Arg Ile Asn
         35                  40                  45

Ser Tyr Val Glu Val Ala Val Asp Gly Leu Pro Ser Glu Thr Lys Lys
     50                  55                  60

Thr Gly Lys Arg Ile Gly Ser Ser Glu Leu Leu Trp Asn Glu Ile Ile
65                  70                  75                  80

Ile Leu Asn Val Thr Ala Gln Ser His Leu Asp Leu Lys Val Trp Ser
                85                  90                  95

Cys His Thr Leu Arg Asn Glu Leu Leu Gly Thr Ala Ser Val Asn Leu
                100                 105                 110

Ser Asn Val Leu Lys Asn Asn Gly Gly Lys Met Glu Asn Met Gln Leu
         115                 120                 125

Thr Leu Asn Leu Gln Thr Glu Asn Lys Gly Ser Val Val Ser Gly Gly
     130                 135                 140

Glu Leu Thr Ile Phe Leu Asp Gly Pro Thr Val Asp Leu Gly Asn Val
145                 150                 155                 160

Pro Asn Gly Ser Ala Leu Thr Asp Gly Ser Gln Leu Pro Ser Arg Asp
                165                 170                 175

Ser Ser Gly Thr Ala Val Ala Pro Glu Asn Arg His Gln Pro Pro Ser
                180                 185                 190

Thr Asn Cys Phe Gly Gly Arg Ser Arg Thr His Arg His Ser Gly Ala
         195                 200                 205

Ser Ala Arg Thr Thr Pro Ala Thr Gly Glu Gln Ser Pro Gly Ala Arg
     210                 215                 220
```

-continued

Ser Arg His Arg Gln Pro Val Lys Asn Ser Gly His Ser Gly Leu Ala
225                 230                 235                 240

Asn Gly Thr Val Asn Asp Glu Pro Thr Thr Ala Thr Asp Pro Glu Glu
            245                 250                 255

Pro Ser Val Val Gly Val Thr Ser Pro Pro Ala Ala Pro Leu Ser Val
            260                 265                 270

Thr Pro Asn Pro Asn Thr Thr Ser Leu Pro Ala Pro Ala Thr Pro Ala
            275                 280                 285

Glu Gly Glu Glu Pro Ser Thr Ser Gly Thr Gln Gln Leu Pro Ala Ala
            290                 295                 300

Ala Gln Ala Pro Asp Ala Leu Pro Ala Gly Trp Glu Gln Arg Glu Leu
305                 310                 315                 320

Pro Asn Gly Arg Val Tyr Tyr Val Asp His Asn Thr Lys Thr Thr Thr
                325                 330                 335

Trp Glu Arg Pro Leu Pro Pro Gly Trp Glu Lys Arg Thr Asp Pro Arg
                340                 345                 350

Gly Arg Phe Tyr Tyr Val Asp His Asn Thr Arg Thr Thr Thr Trp Gln
            355                 360                 365

Arg Pro Thr Ala Glu Tyr Val Arg Asn Tyr Glu Gln Trp Gln Ser Gln
370                 375                 380

Arg Asn Gln Leu Gln Gly Ala Met Gln His Phe Ser Gln Arg Phe Leu
385                 390                 395                 400

Tyr Gln Ser Ser Ser Ala Ser Thr Asp His Asp Pro Leu Gly Pro Leu
                405                 410                 415

Pro Pro Gly Trp Glu Lys Arg Gln Asp Asn Gly Arg Val Tyr Tyr Val
            420                 425                 430

Asn His Asn Thr Arg Thr Thr Gln Trp Glu Asp Pro Arg Thr Gln Gly
            435                 440                 445

Met Ile Gln Glu Pro Ala Leu Pro Pro Gly Trp Glu Met Lys Tyr Thr
450                 455                 460

Ser Glu Gly Val Arg Tyr Phe Val Asp His Asn Thr Arg Thr Thr Thr
465                 470                 475                 480

Phe Lys Asp Pro Arg Pro Gly Phe Glu Ser Gly Thr Lys Gln Gly Ser
                485                 490                 495

Pro Gly Ala Tyr Asp Arg Ser Phe Arg Trp Lys Tyr His Gln Phe Arg
            500                 505                 510

Phe Leu Cys His Ser Asn Ala Leu Pro Ser His Val Lys Ile Ser Val
            515                 520                 525

Ser Arg Gln Thr Leu Phe Glu Asp Ser Phe Gln Gln Ile Met Asn Met
530                 535                 540

Lys Pro Tyr Asp Leu Arg Arg Arg Leu Tyr Ile Ile Met Arg Gly Glu
545                 550                 555                 560

Glu Gly Leu Asp Tyr Gly Gly Ile Ala Arg Glu Trp Phe Phe Leu Leu
                565                 570                 575

Ser His Glu Val Leu Asn Pro Met Tyr Cys Leu Phe Glu Tyr Ala Gly
            580                 585                 590

Lys Asn Asn Tyr Cys Leu Gln Ile Asn Pro Ala Ser Ser Ile Asn Pro
            595                 600                 605

Asp His Leu Thr Tyr Phe Arg Phe Ile Gly Arg Phe Ile Ala Met Ala
            610                 615                 620

Leu Tyr His Gly Lys Phe Ile Asp Thr Gly Phe Thr Leu Pro Phe Tyr
625                 630                 635                 640

```
Lys Arg Met Leu Asn Lys Arg Pro Thr Leu Lys Asp Leu Glu Ser Ile
                645                 650                 655

Asp Pro Glu Phe Tyr Asn Ser Ile Val Trp Ile Lys Glu Asn Asn Leu
            660                 665                 670

Glu Glu Cys Gly Leu Glu Leu Tyr Phe Ile Gln Asp Met Glu Ile Leu
        675                 680                 685

Gly Lys Val Thr Thr His Glu Leu Lys Glu Gly Glu Ser Ile Arg
    690                 695                 700

Val Thr Glu Glu Asn Lys Glu Tyr Ile Met Leu Leu Thr Asp Trp
705                 710                 715                 720

Arg Phe Thr Arg Gly Val Glu Glu Gln Thr Lys Ala Phe Leu Asp Gly
                725                 730                 735

Phe Asn Glu Val Ala Pro Leu Glu Trp Leu Arg Tyr Phe Asp Glu Lys
            740                 745                 750

Glu Leu Glu Leu Met Leu Cys Gly Met Gln Glu Ile Asp Met Ser Asp
        755                 760                 765

Trp Gln Lys Ser Thr Ile Tyr Arg His Tyr Thr Lys Asn Ser Lys Gln
    770                 775                 780

Ile Gln Trp Phe Trp Gln Val Val Lys Glu Met Asp Asn Glu Lys Arg
785                 790                 795                 800

Ile Arg Leu Leu Gln Phe Val Thr Gly Thr Cys Arg Leu Pro Val Gly
                805                 810                 815

Gly Phe Ala Glu Leu Ile Gly Ser Asn Gly Pro Gln Lys Phe Cys Ile
            820                 825                 830

Asp Lys Val Gly Lys Glu Thr Trp Leu Pro Arg Ser His Thr Cys Phe
        835                 840                 845

Asn Arg Leu Asp Leu Pro Pro Tyr Lys Ser Tyr Glu Gln Leu Arg Glu
    850                 855                 860

Lys Leu Leu Tyr Ala Ile Glu Glu Thr Glu Gly Phe Gly Gln Glu
865                 870                 875

<210> SEQ ID NO 24
<211> LENGTH: 922
<212> TYPE: PRT
<213> ORGANISM: Artificial Sequence
<220> FEATURE:
<223> OTHER INFORMATION: WWP1 PEPTIDE SEQUENCE

<400> SEQUENCE: 24

Met Ala Thr Ala Ser Pro Arg Ser Asp Thr Ser Asn Asn His Ser Gly
1               5                   10                  15

Arg Leu Gln Leu Gln Val Thr Val Ser Ser Ala Lys Leu Lys Arg Lys
                20                  25                  30

Lys Asn Trp Phe Gly Thr Ala Ile Tyr Thr Glu Val Val Val Asp Gly
            35                  40                  45

Glu Ile Thr Lys Thr Ala Lys Ser Ser Ser Ser Asn Pro Lys Trp
    50                  55                  60

Asp Glu Gln Leu Thr Val Asn Val Thr Pro Gln Thr Thr Leu Glu Phe
65                  70                  75                  80

Gln Val Trp Ser His Arg Thr Leu Lys Ala Asp Ala Leu Leu Gly Lys
                85                  90                  95

Ala Thr Ile Asp Leu Lys Gln Ala Leu Leu Ile His Asn Arg Lys Leu
            100                 105                 110

Glu Arg Val Lys Glu Gln Leu Lys Leu Ser Leu Glu Asn Lys Asn Gly
        115                 120                 125
```

```
Ile Ala Gln Thr Gly Glu Leu Thr Val Val Leu Asp Gly Leu Val Ile
130                 135                 140
Glu Gln Glu Asn Ile Thr Asn Cys Ser Ser Pro Thr Ile Glu Ile
145                 150                 155                 160
Gln Glu Asn Gly Asp Ala Leu His Glu Asn Gly Glu Pro Ser Ala Arg
                165                 170                 175
Thr Thr Ala Arg Leu Ala Val Glu Gly Thr Asn Gly Ile Asp Asn His
                180                 185                 190
Val Pro Thr Ser Thr Leu Val Gln Asn Ser Cys Cys Ser Tyr Val Val
            195                 200                 205
Asn Gly Asp Asn Thr Pro Ser Ser Pro Ser Gln Val Ala Ala Arg Pro
210                 215                 220
Lys Asn Thr Pro Ala Pro Lys Pro Leu Ala Ser Glu Pro Ala Asp Asp
225                 230                 235                 240
Thr Val Asn Gly Glu Ser Ser Ser Phe Ala Pro Thr Asp Asn Ala Ser
                245                 250                 255
Val Thr Gly Thr Pro Val Val Ser Glu Glu Asn Ala Leu Ser Pro Asn
                260                 265                 270
Cys Thr Ser Thr Thr Val Glu Asp Pro Pro Val Gln Glu Ile Leu Thr
            275                 280                 285
Ser Ser Glu Asn Asn Glu Cys Ile Pro Ser Thr Ser Ala Glu Leu Glu
290                 295                 300
Ser Glu Ala Arg Ser Ile Leu Glu Pro Asp Thr Ser Asn Ser Arg Ser
305                 310                 315                 320
Ser Ser Ala Phe Glu Ala Ala Lys Ser Arg Gln Pro Asp Gly Cys Met
                325                 330                 335
Asp Pro Val Arg Gln Gln Ser Gly Asn Ala Asn Thr Glu Thr Leu Pro
            340                 345                 350
Ser Gly Trp Glu Gln Arg Lys Asp Pro His Gly Arg Thr Tyr Tyr Val
            355                 360                 365
Asp His Asn Thr Arg Thr Thr Thr Trp Glu Arg Pro Gln Pro Leu Pro
            370                 375                 380
Pro Gly Trp Glu Arg Arg Val Asp Asp Arg Arg Arg Val Tyr Tyr Val
385                 390                 395                 400
Asp His Asn Thr Arg Thr Thr Thr Trp Gln Arg Pro Thr Met Glu Ser
                405                 410                 415
Val Arg Asn Phe Glu Gln Trp Gln Ser Gln Arg Asn Gln Leu Gln Gly
                420                 425                 430
Ala Met Gln Gln Phe Asn Gln Arg Tyr Leu Tyr Ser Ala Ser Met Leu
            435                 440                 445
Ala Ala Glu Asn Asp Pro Tyr Gly Pro Leu Pro Pro Gly Trp Glu Lys
450                 455                 460
Arg Val Asp Ser Thr Asp Arg Val Tyr Phe Val Asn His Asn Thr Lys
465                 470                 475                 480
Thr Thr Gln Trp Glu Asp Pro Arg Thr Gln Gly Leu Gln Asn Glu Glu
                485                 490                 495
Pro Leu Pro Glu Gly Trp Glu Ile Arg Tyr Thr Arg Glu Gly Val Arg
            500                 505                 510
Tyr Phe Val Asp His Asn Thr Arg Thr Thr Thr Phe Lys Asp Pro Arg
            515                 520                 525
Asn Gly Lys Ser Ser Val Thr Lys Gly Gly Pro Gln Ile Ala Tyr Glu
530                 535                 540
Arg Gly Phe Arg Trp Lys Leu Ala His Phe Arg Tyr Leu Cys Gln Ser
```

```
            545                 550                 555                 560
Asn Ala Leu Pro Ser His Val Lys Ile Asn Val Ser Arg Gln Thr Leu
                565                 570                 575

Phe Glu Asp Ser Phe Gln Gln Ile Met Ala Leu Lys Pro Tyr Asp Leu
                580                 585                 590

Arg Arg Arg Leu Tyr Val Ile Phe Arg Gly Glu Gly Leu Asp Tyr
                595                 600                 605

Gly Gly Leu Ala Arg Glu Trp Phe Phe Leu Leu Ser His Glu Val Leu
    610                 615                 620

Asn Pro Met Tyr Cys Leu Phe Glu Tyr Ala Gly Lys Asn Asn Tyr Cys
625                 630                 635                 640

Leu Gln Ile Asn Pro Ala Ser Thr Ile Asn Pro Asp His Leu Ser Tyr
                645                 650                 655

Phe Cys Phe Ile Gly Arg Phe Ile Ala Met Ala Leu Phe His Gly Lys
                660                 665                 670

Phe Ile Asp Thr Gly Phe Ser Leu Pro Phe Tyr Lys Arg Met Leu Ser
                675                 680                 685

Lys Lys Leu Thr Ile Lys Asp Leu Glu Ser Ile Asp Thr Glu Phe Tyr
            690                 695                 700

Asn Ser Leu Ile Trp Ile Arg Asp Asn Asn Ile Glu Glu Cys Gly Leu
705                 710                 715                 720

Glu Met Tyr Phe Ser Val Asp Met Glu Ile Leu Gly Lys Val Thr Ser
                725                 730                 735

His Asp Leu Lys Leu Gly Gly Ser Asn Ile Leu Val Thr Glu Glu Asn
                740                 745                 750

Lys Asp Glu Tyr Ile Gly Leu Met Thr Glu Trp Arg Phe Ser Arg Gly
            755                 760                 765

Val Gln Glu Gln Thr Lys Ala Phe Leu Asp Gly Phe Asn Glu Val Val
        770                 775                 780

Pro Leu Gln Trp Leu Gln Tyr Phe Asp Glu Lys Glu Leu Glu Val Met
785                 790                 795                 800

Leu Cys Gly Met Gln Glu Val Asp Leu Ala Asp Trp Gln Arg Asn Thr
                805                 810                 815

Val Tyr Arg His Tyr Thr Arg Asn Ser Lys Gln Ile Ile Trp Phe Trp
                820                 825                 830

Gln Phe Val Lys Glu Thr Asp Asn Glu Val Arg Met Arg Leu Leu Gln
                835                 840                 845

Phe Val Thr Gly Thr Cys Arg Leu Pro Leu Gly Gly Phe Ala Glu Leu
                850                 855                 860

Met Gly Ser Asn Gly Pro Gln Lys Phe Cys Ile Glu Lys Val Gly Lys
865                 870                 875                 880

Asp Thr Trp Leu Pro Arg Ser His Thr Cys Phe Asn Arg Leu Asp Leu
                885                 890                 895

Pro Pro Tyr Lys Ser Tyr Glu Gln Leu Lys Glu Lys Leu Leu Phe Ala
                900                 905                 910

Ile Glu Glu Thr Glu Gly Phe Gly Gln Glu
            915                 920

<210> SEQ ID NO 25
<211> LENGTH: 390
<212> TYPE: PRT
<213> ORGANISM: Artificial Sequence
<220> FEATURE:
<223> OTHER INFORMATION: TSG101 PROTEIN SEQUENCE
```

<400> SEQUENCE: 25

```
Met Ala Val Ser Glu Ser Gln Leu Lys Lys Met Val Ser Lys Tyr Lys
1               5                   10                  15

Tyr Arg Asp Leu Thr Val Arg Glu Thr Val Asn Val Ile Thr Leu Tyr
            20                  25                  30

Lys Asp Leu Lys Pro Val Leu Asp Ser Tyr Val Phe Asn Asp Gly Ser
        35                  40                  45

Ser Arg Glu Leu Met Asn Leu Thr Gly Thr Ile Pro Val Pro Tyr Arg
    50                  55                  60

Gly Asn Thr Tyr Asn Ile Pro Ile Cys Leu Trp Leu Leu Asp Thr Tyr
65                  70                  75                  80

Pro Tyr Asn Pro Pro Ile Cys Phe Val Lys Pro Thr Ser Ser Met Thr
                85                  90                  95

Ile Lys Thr Gly Lys His Val Asp Ala Asn Gly Lys Ile Tyr Leu Pro
            100                 105                 110

Tyr Leu His Glu Trp Lys His Pro Gln Ser Asp Leu Leu Gly Leu Ile
        115                 120                 125

Gln Val Met Ile Val Val Phe Gly Asp Glu Pro Pro Val Phe Ser Arg
    130                 135                 140

Pro Ile Ser Ala Ser Tyr Pro Pro Tyr Gln Ala Thr Gly Pro Pro Asn
145                 150                 155                 160

Thr Ser Tyr Met Pro Gly Met Pro Gly Gly Ile Ser Pro Tyr Pro Ser
                165                 170                 175

Gly Tyr Pro Pro Asn Pro Ser Gly Tyr Pro Gly Cys Pro Tyr Pro Pro
            180                 185                 190

Gly Gly Pro Tyr Pro Ala Thr Thr Ser Ser Gln Tyr Pro Ser Gln Pro
        195                 200                 205

Pro Val Thr Thr Val Gly Pro Ser Arg Asp Gly Thr Ile Ser Glu Asp
    210                 215                 220

Thr Ile Arg Ala Ser Leu Ile Ser Ala Val Ser Asp Lys Leu Arg Trp
225                 230                 235                 240

Arg Met Lys Glu Glu Met Asp Arg Ala Gln Ala Glu Leu Asn Ala Leu
                245                 250                 255

Lys Arg Thr Glu Glu Asp Leu Lys Lys Gly His Gln Lys Leu Glu Glu
            260                 265                 270

Met Val Thr Arg Leu Asp Gln Glu Val Ala Glu Val Asp Lys Asn Ile
        275                 280                 285

Glu Leu Leu Lys Lys Lys Asp Glu Glu Leu Ser Ser Ala Leu Glu Lys
    290                 295                 300

Met Glu Asn Gln Ser Glu Asn Asn Asp Ile Asp Glu Val Ile Ile Pro
305                 310                 315                 320

Thr Ala Pro Leu Tyr Lys Gln Ile Leu Asn Leu Tyr Ala Glu Glu Asn
                325                 330                 335

Ala Ile Glu Asp Thr Ile Phe Tyr Leu Gly Glu Ala Leu Arg Arg Gly
            340                 345                 350

Val Ile Asp Leu Asp Val Phe Leu Lys His Val Arg Leu Leu Ser Arg
        355                 360                 365

Lys Gln Phe Gln Leu Arg Ala Leu Met Gln Lys Ala Arg Lys Thr Ala
    370                 375                 380

Gly Leu Ser Asp Leu Tyr
385                 390
```

<210> SEQ ID NO 26

```
<211> LENGTH: 174
<212> TYPE: PRT
<213> ORGANISM: Artificial Sequence
<220> FEATURE:
<223> OTHER INFORMATION: TRUNCATED-LENGTH TSG101 RECOMBINANT PEPTIDE

<400> SEQUENCE: 26

Met Gly Ser Ser His His His His His His Ser Ser Gly Leu Val Pro
1               5                   10                  15

Arg Gly Ser His Met Ala Ser Glu Asn Leu Tyr Phe Gln Gly Ala Val
            20                  25                  30

Ser Glu Ser Gln Leu Lys Lys Met Val Ser Lys Tyr Lys Tyr Arg Asp
        35                  40                  45

Leu Thr Val Arg Glu Thr Val Asn Val Ile Thr Leu Tyr Lys Asp Leu
    50                  55                  60

Lys Pro Val Leu Asp Ser Tyr Val Phe Asn Asp Gly Ser Ser Arg Glu
65                  70                  75                  80

Leu Met Asn Leu Thr Gly Thr Ile Pro Val Pro Tyr Arg Gly Asn Thr
                85                  90                  95

Tyr Asn Ile Pro Ile Cys Leu Trp Leu Leu Asp Thr Tyr Pro Tyr Asn
            100                 105                 110

Pro Pro Ile Cys Phe Val Lys Pro Thr Ser Ser Met Thr Ile Lys Thr
        115                 120                 125

Gly Lys His Val Asp Ala Asn Gly Lys Ile Tyr Leu Pro Tyr Leu His
    130                 135                 140

Glu Trp Lys His Pro Gln Ser Asp Leu Leu Gly Leu Ile Gln Val Met
145                 150                 155                 160

Ile Val Val Phe Gly Asp Glu Pro Pro Val Phe Ser Arg Pro
                165                 170
```